US008043843B2

(12) United States Patent (10) Patent No.: US 8,043,843 B2
Nilsson (45) Date of Patent: Oct. 25, 2011

(54) METABOLICALLY ENGINEERED LACTIC ACID BACTERIA AND THEIR USE

(76) Inventor: Dan Nilsson, Espergaerde (DK)

( * ) Notice: Subject to any disclaimer, the term of this patent is extended or adjusted under 35 U.S.C. 154(b) by 146 days.

(21) Appl. No.: 12/332,442

(22) Filed: Dec. 11, 2008

(65) Prior Publication Data

US 2009/0155411 A1 Jun. 18, 2009

Related U.S. Application Data

(60) Division of application No. 10/658,376, filed on Sep. 10, 2003, now Pat. No. 7,465,575, which is a division of application No. 08/981,098, filed as application No. PCT/DK97/00335 on Aug. 20, 1997, now Pat. No. 6,645,754, which is a continuation-in-part of application No. 08/701,459, filed on Aug. 22, 1996, now abandoned.

(51) Int. Cl.
*C12N 1/20* (2006.01)
*C12N 1/00* (2006.01)
*A01N 63/00* (2006.01)

(52) U.S. Cl. .................. 435/252.9; 435/252.1; 435/853; 424/93.45

(58) Field of Classification Search ........................ None
See application file for complete search history.

(56) References Cited

OTHER PUBLICATIONS

Hugenholtz J. "Citrate metabolism in lactic bacteria". FEMS Microbiology Reviews. 1993, 12, pp. 165-178.*
Takahashi et al. "Oxygen sensitivity of sugar metabolism and interconversion of pyruvate formate lyase in intact cells of *Streptococus mutans* and *Streptococcus sanguis*". Infection and Immunity. Mar. 1987. vol. 55, No. 3, pp. 652-656.
Yamamoto et al. Cloning and sequence analysis of the pfl gene encoding private formate lyases from *Streptococus mutans*. Infection and Immunity. Feb. 1996, vol. 64, No. 2, pp. 385-391.
Böck, et al., *Fermentation, Escherichia coli* and *Salmonella*, Cellular and Molecular Biology, (Eds. in Chief Frederick C. Neidhardt), ASM Press, Washington, D.C., pp. 262-282, 1996.
Bolotin, et al., *Low-redundancy sequencing of the entire Lactococcus lactis IL1403 genome*, Antonie Van Leeuwenhoek, vol. 76, pp. 27-76, 1999.
Cogan, et al, *Impact of aeration on the metabolic end-products formed from glucose and galactose by Streptococcus lactis*, Journal of Applied Bacteriology, vol. 66, pp. 77-84, 1989.
Collins, et a., *Roles of Acetate and Pyruvate in the Metabolism of Streptococcus diacetilactis*, Journal of Bacteriology, vol. 103, No. 3, pp. 541-546, 1970.
Cronan, et al., *Tricarboxylic Acid Cycle and Glyoxylate Bybass, Escherichia coli* and *Salmonella* Cellular and Molecular Biology (Eds. in Chief Frederick C. Neidhardt, ASM Press, Washington, D.C., pp. 206-216, 1996.
Gennis, et al., *Respiration, Escherichia coli* and *Salmonella* Cellular and Molecular Biology (Eds. in Chief Frederic C. Neidhardt, ASM Press, Washington, D.C., pp. 217-261, 1996.
Neidhardt, *The Enteric Bacterial Cell and the Age of Bacteria, Escherichia* and *Salmonella* Cellular and Molecular Biology (Eds. in Chief Frederic C. Neidhardt, ASM Press, Washington, D.C., pp. 1-3, 1996.
Reed, et al., *Acetate-Replacing Factors for Lactic Acid Bacteria*, J. Biol. Chem. vol. 162, pp. 851-858, 1951.
Reiter, et al., *Nutritional studies on cheese starters*, J. Dairy Res., vol. 29, pp. 63-77, 1962.
Snoep, et al., *Differences in sensitivity to NADH of purified pyruvate dehydrogenase complexes of Enterococcus faecalis, Lactococcus lactis, Axotobacter vinelandii and Escherichia coli: Implications of their activity in vivo*, FEMS Microbiology Letters, vol. 114, pp. 279-283, 1993.
Takahashi, et al., *Oxygen Sensitivity of Sugar Metabolism and Interconversion of Pyruvate Formate-Lyase in Intact Cells of Streptococcus mutans and Streptococcus sanguis*, Infection and Immunity, vol. 55, No. 3, pp. 652-656, 1987.
Takahashi, et al., *Purification of Pyruvate Formate-Lyase from Streptococcus mutans and Its Regulatory Properties*, Journal of Bacteriology, vol. 149, No. 3, pp. 1034-1040, Mar. 1982.
Takahashi et al. Oral Microbiology and Immunology. 1995. vol. 10, pp. 349-354.
McKay, et al., *Altered Metablism in a Streptococcus lactis C2 Mutant Deficient in Lactic Dehydrogenase*, Journal of Dairy Science, vol. 57, No. 2, pp. 181-186, 1973.
Dickely, Francoise et al., "Isolation of *Lactococcus lactis* nonsense suppressors and construction of a food-grade cloning vector." Molecular Microbiology, vol. 15, No. 5, pp. 839-847 (1995).
Gasson, M.J. et at., "Metabolic engineering of the *Lactococcus lactic* diacetyl pathway.", LAIT, vol. 76, pp. 33-40 (1996).
"HPLC analysis determination of acids and carbohydrates in liquid fermentation media using internal standard.", Chr. Hansen's Laboratorium Danmark A/S, Analytical Procedure AP1009 (1993).
"HSGC—In situ derivation of acids in fermentates for physiological investigations." Chr. Hansen's, Technical Report TR 785, (1995).
"HSGC—Determination of volatile organic compounds and α-aceto lactic acid.", CHR's Hansen, Analytical Procedure AP 1048, (1995).
Hugenholtz, Jeroen, "Citrate metabolism in lactic acid bacteria.", FEMS Microbiology Reviews, vol. 12, pp. 165-178 (1993).
Knappe, Joachim "Anaerobic dissimilation of pyruvate.", Institute for Chemical Biology, No. 13, pp. 151-155, 1985.
Platteeuw, Christ et al., "Metabolic engineering of *Lactococcus lactis*: Influence of the overproduction of α-acetolactate synthase in strains deficient in lactate dehydrogenase as a function of culture conditions" Applied and Environmental Microbiology, pp. 3967-3971, 1995.
Snoep, Jacob., "Regulation of pyruvate catabolism in *Enterococcus faecalis*: A molecular approach to physiology.", Academisch Proefschrift, Chp. 1-4, pp. 1-92 (1992).

(Continued)

*Primary Examiner* — Vera Afremova
(74) *Attorney, Agent, or Firm* — Iver P. Cooper

(57) ABSTRACT

Mutants of lactic acid bacteria including *Lactococcus lactis* which are defective in pyruvate formate-lyase production and/or in their lactate dehydrogenase (Ldh) production and methods of isolating such mutants or variants are provided. The mutants are useful in the production of food products or in manufacturing of compounds such as diacetyl, acetoin and acetaldehyde and as components of food starter cultures.

16 Claims, 17 Drawing Sheets

OTHER PUBLICATIONS

Figure 1:
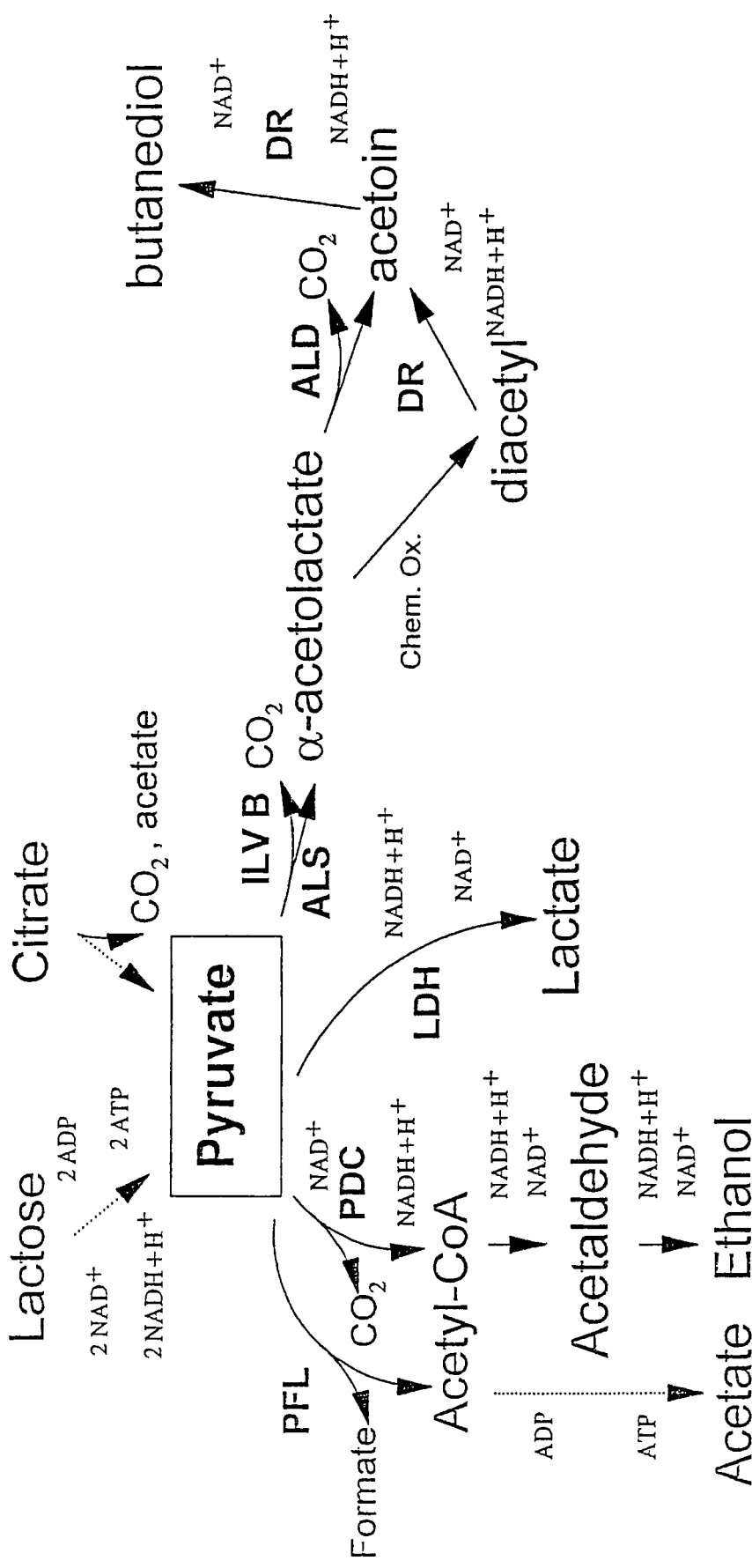
Figure 2A:
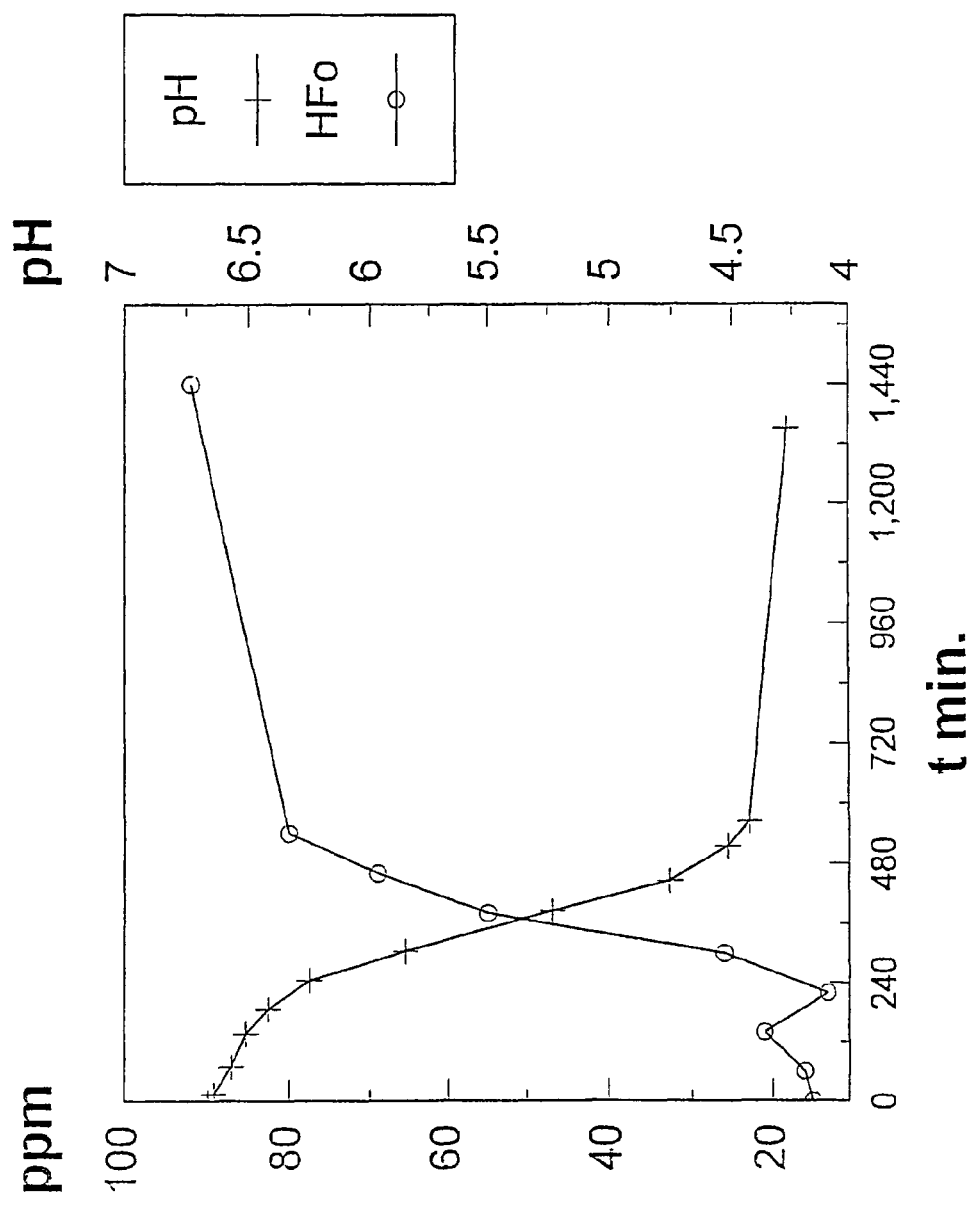
Figure 2B:
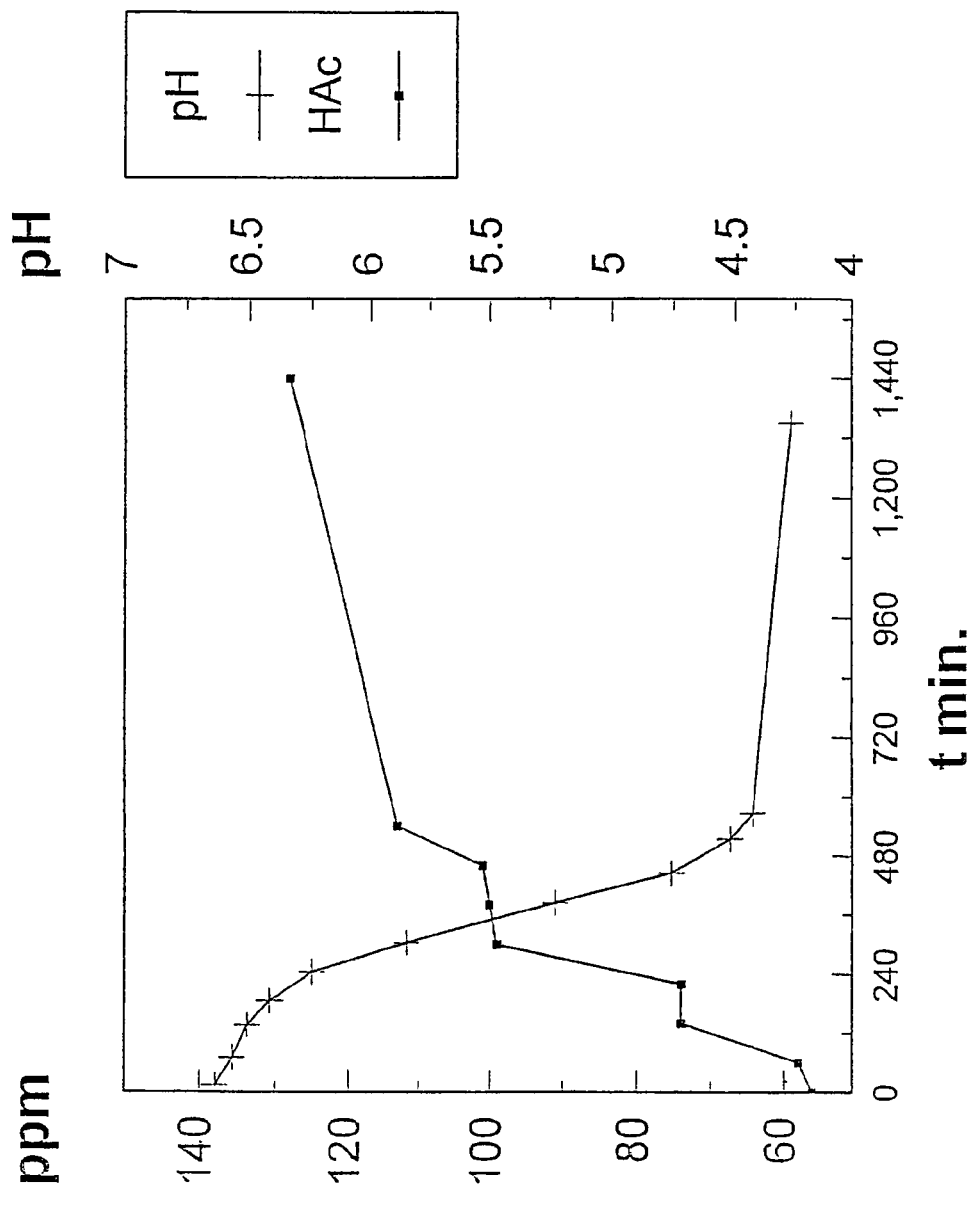
Figure 2C:
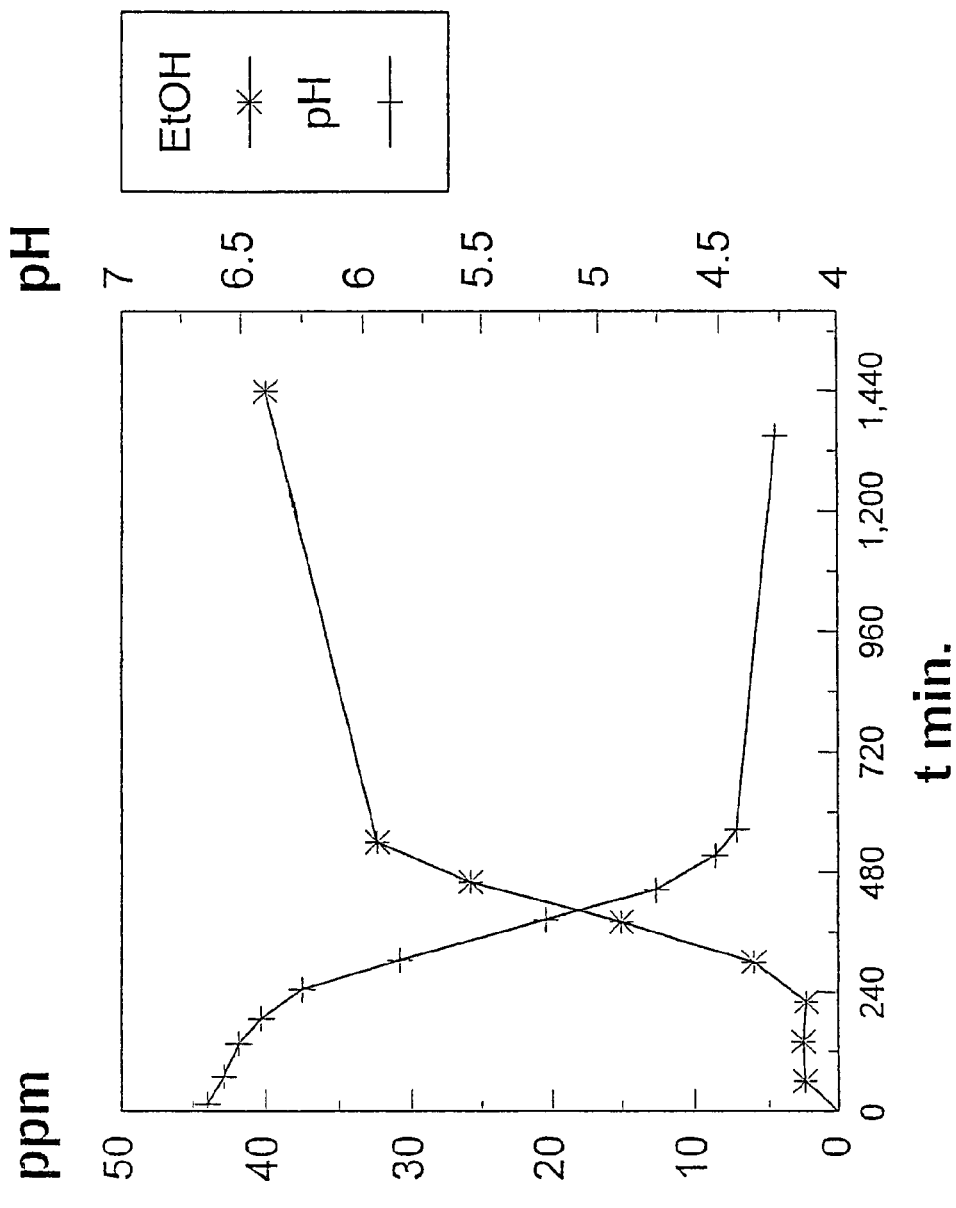
Figure 2D:
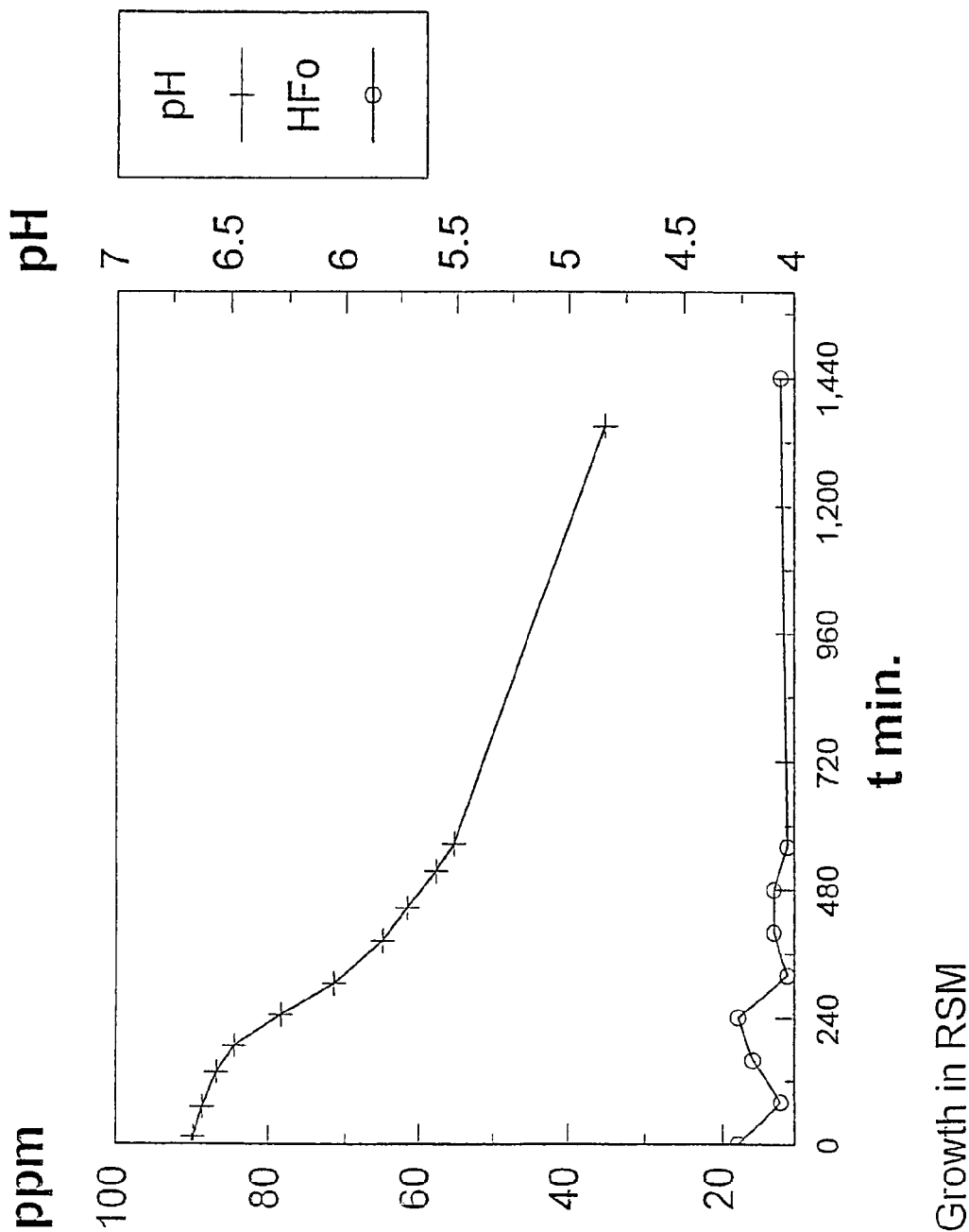
Figure 2E:
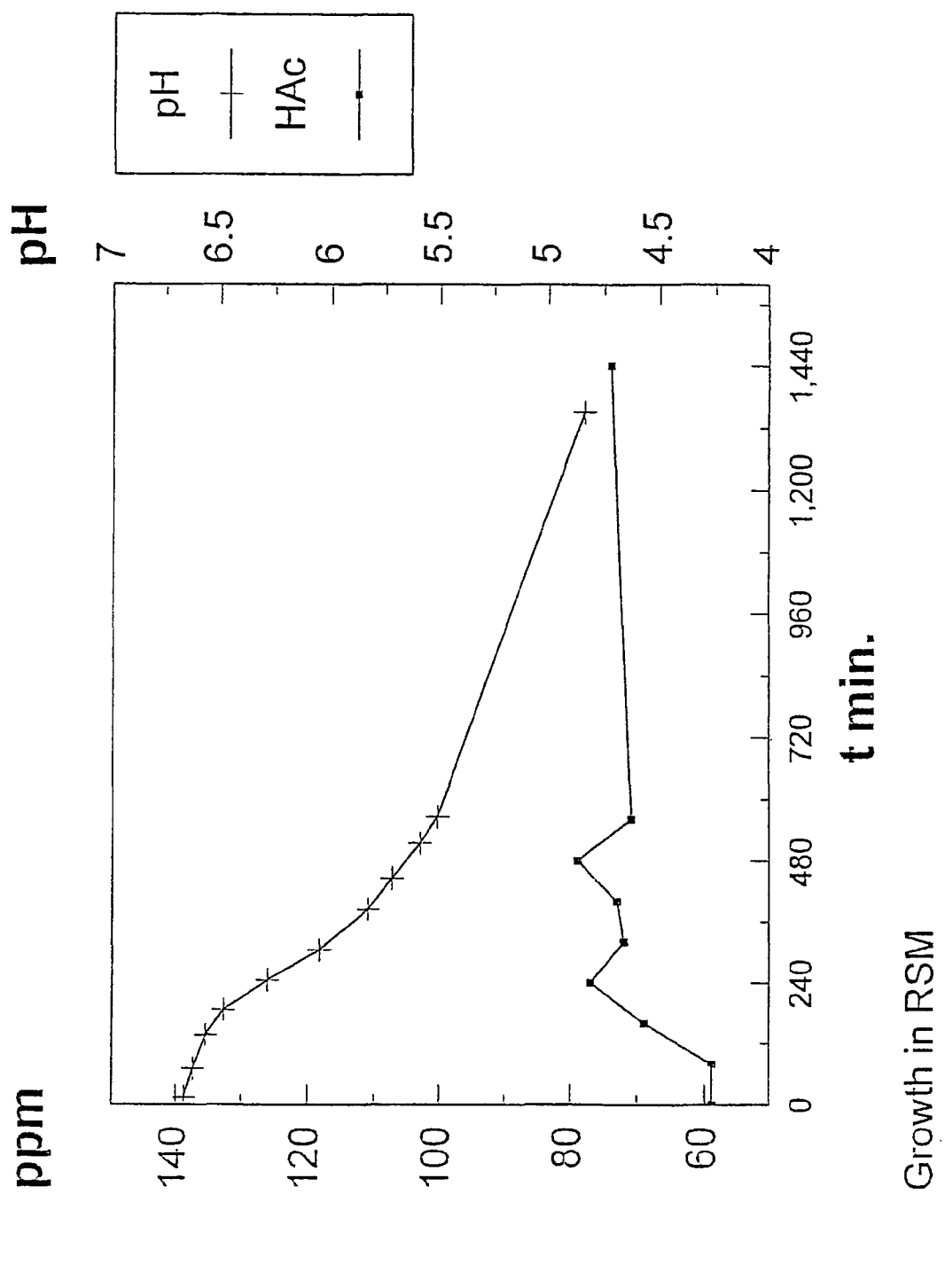
Figure 2F:
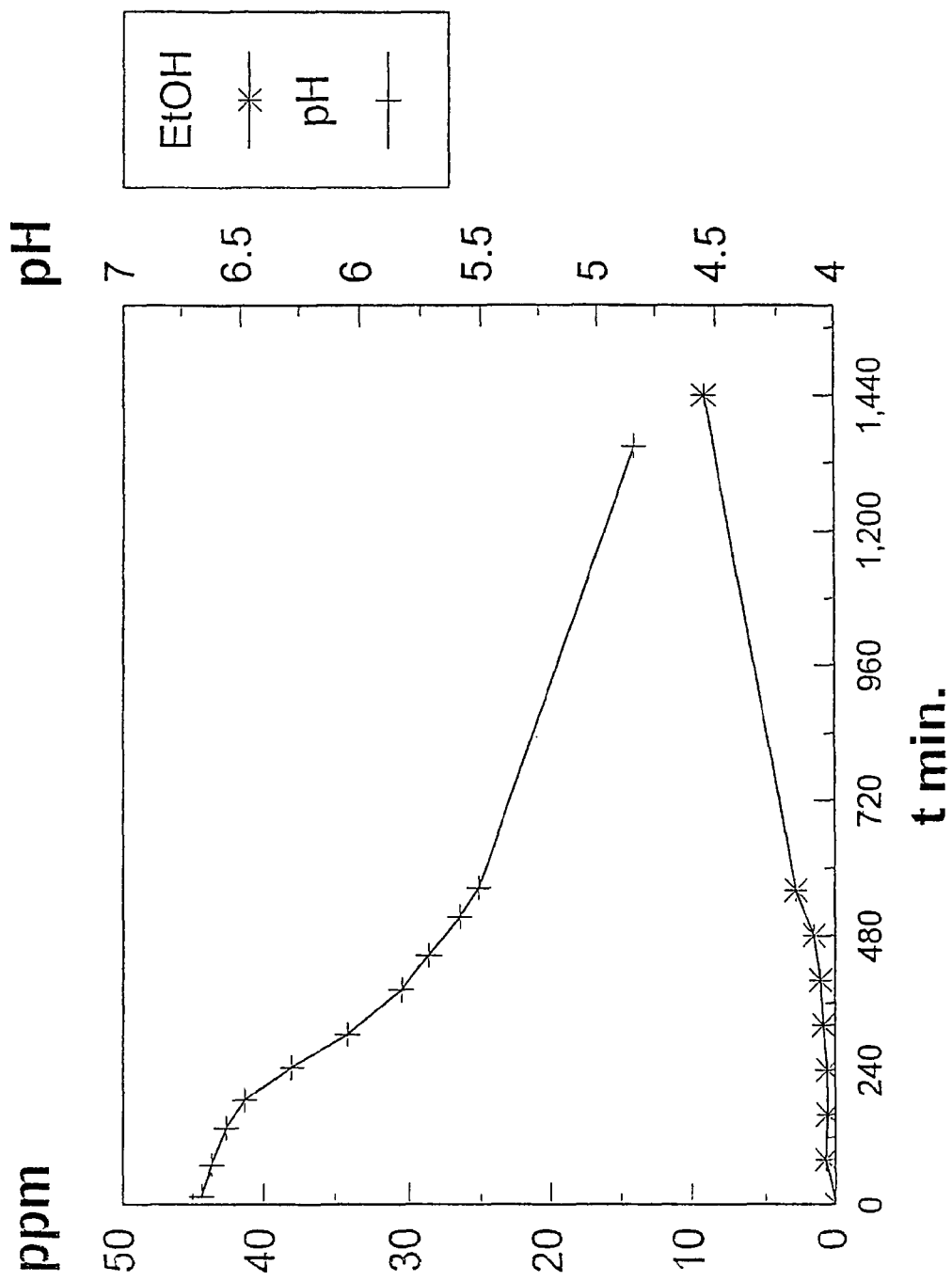
Figure 3A:
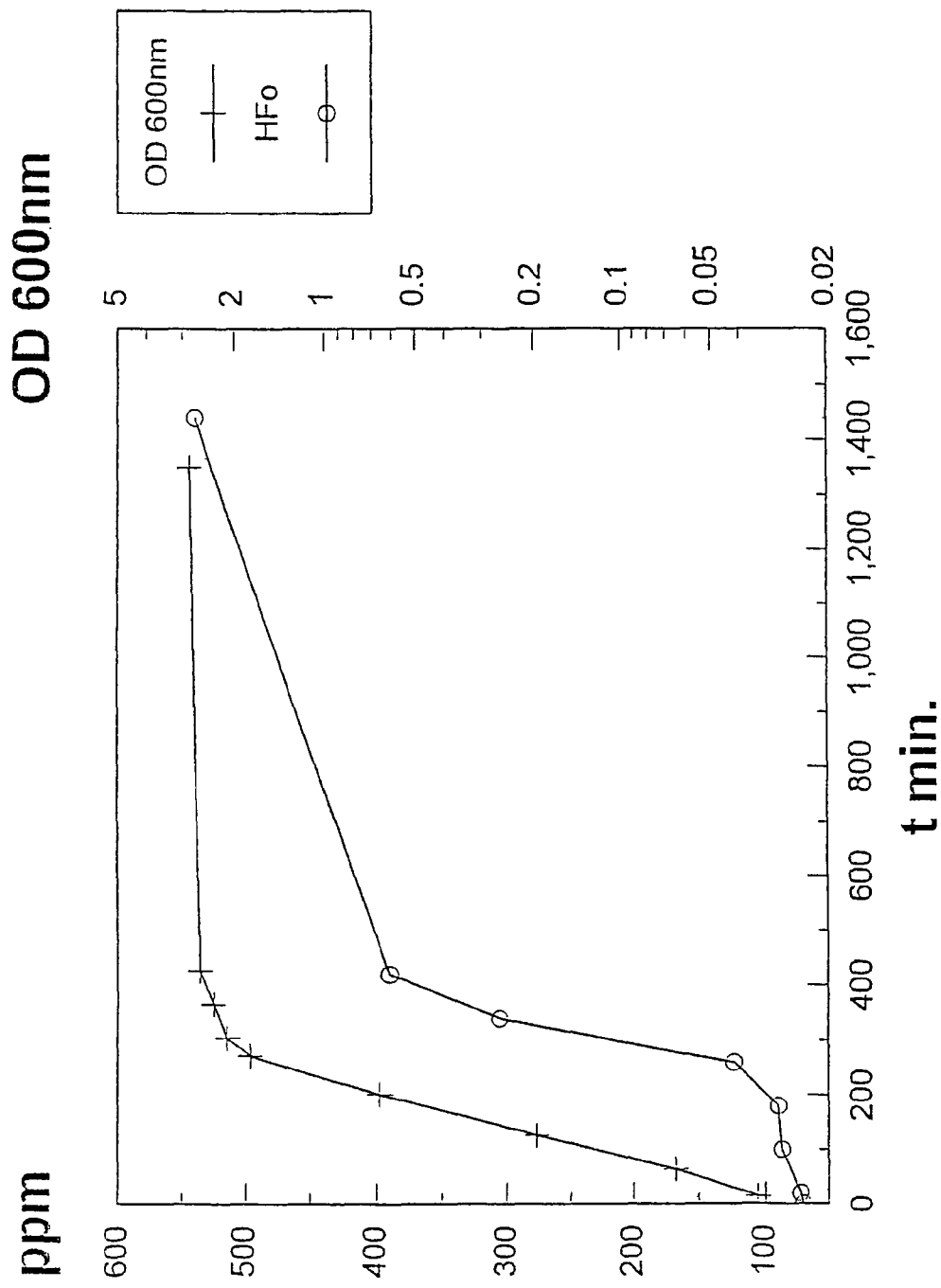
Figure 3B:
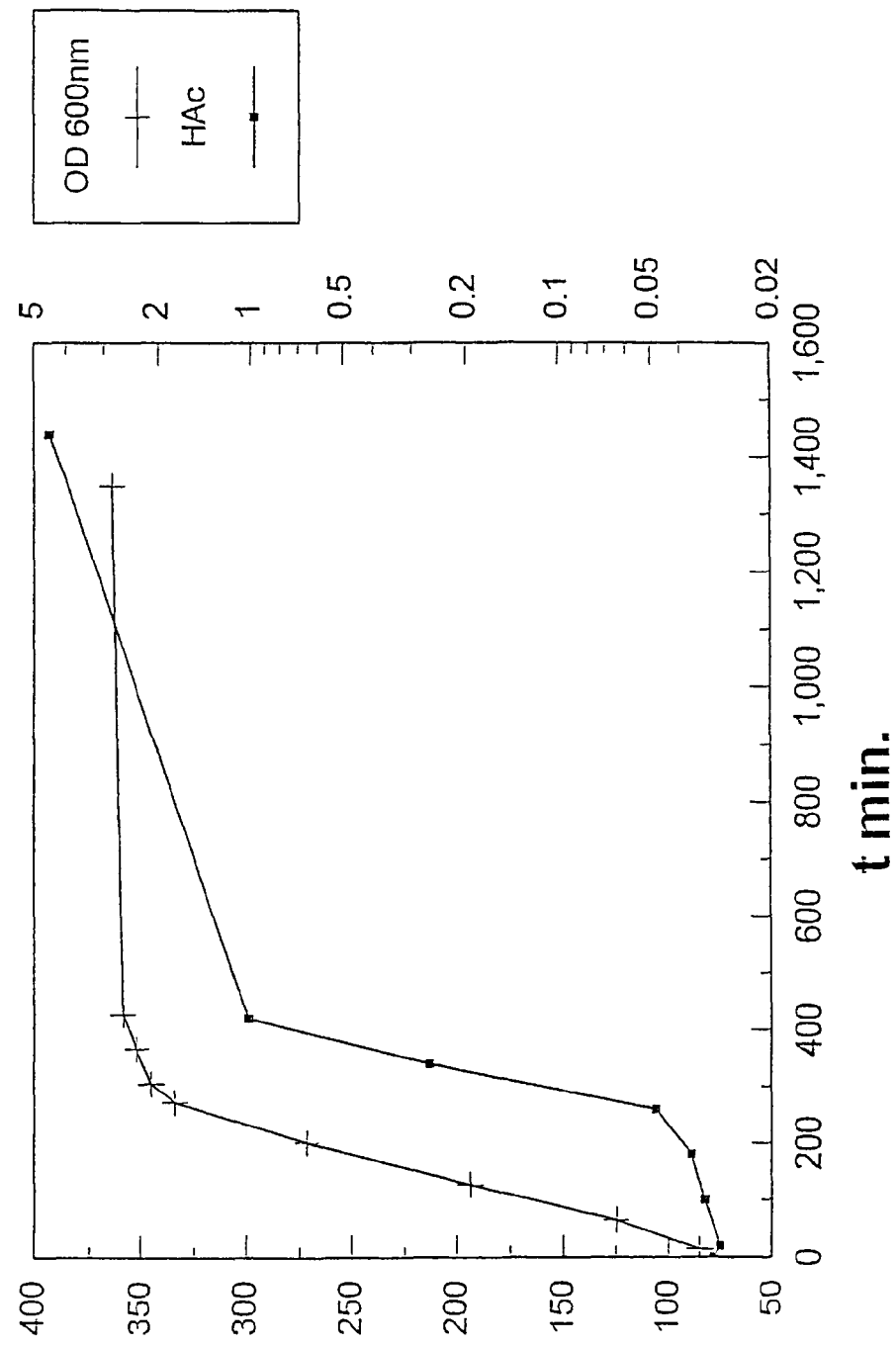
Figure 3C:
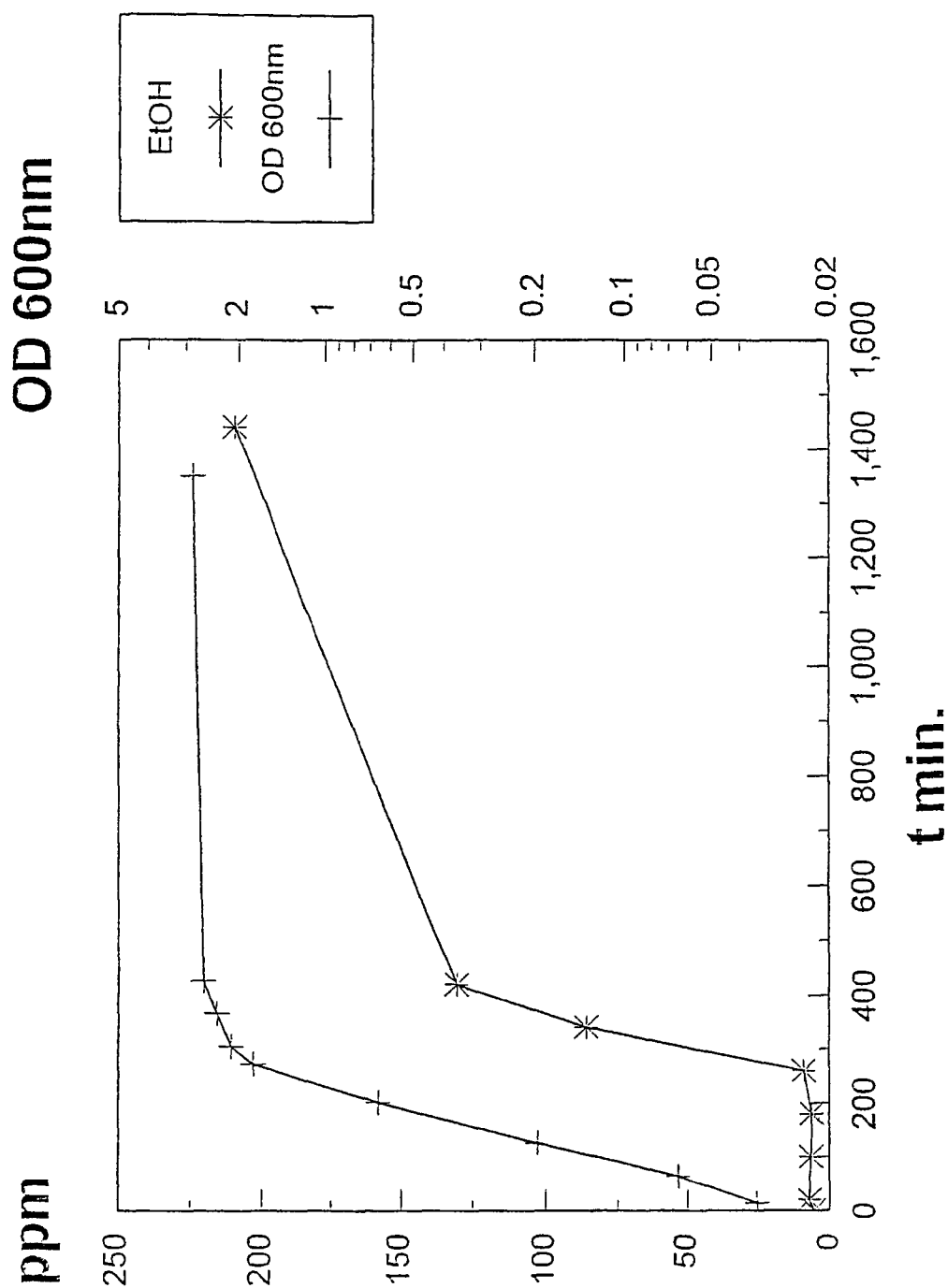
Figure 3D:
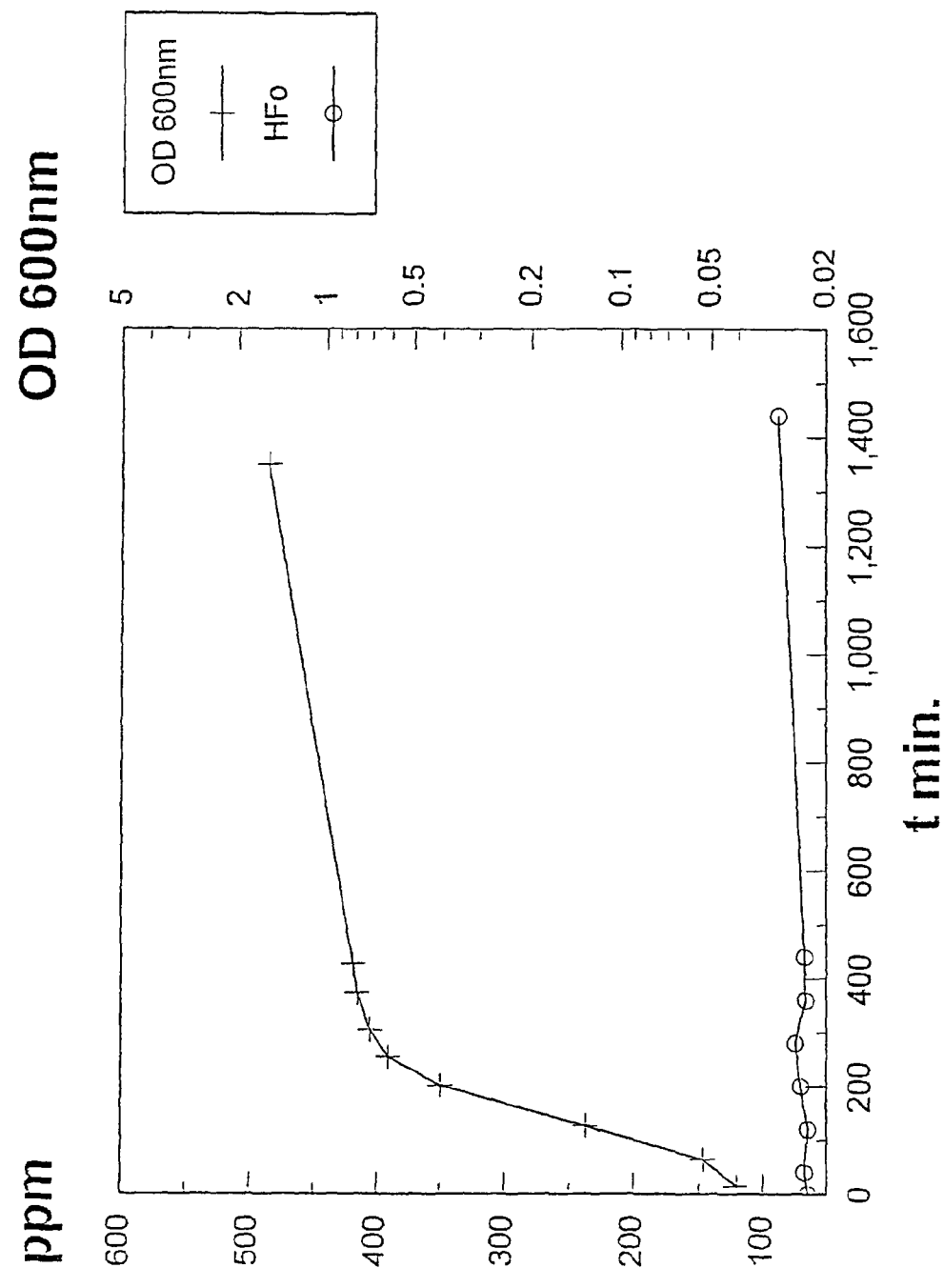
Figure 3E:
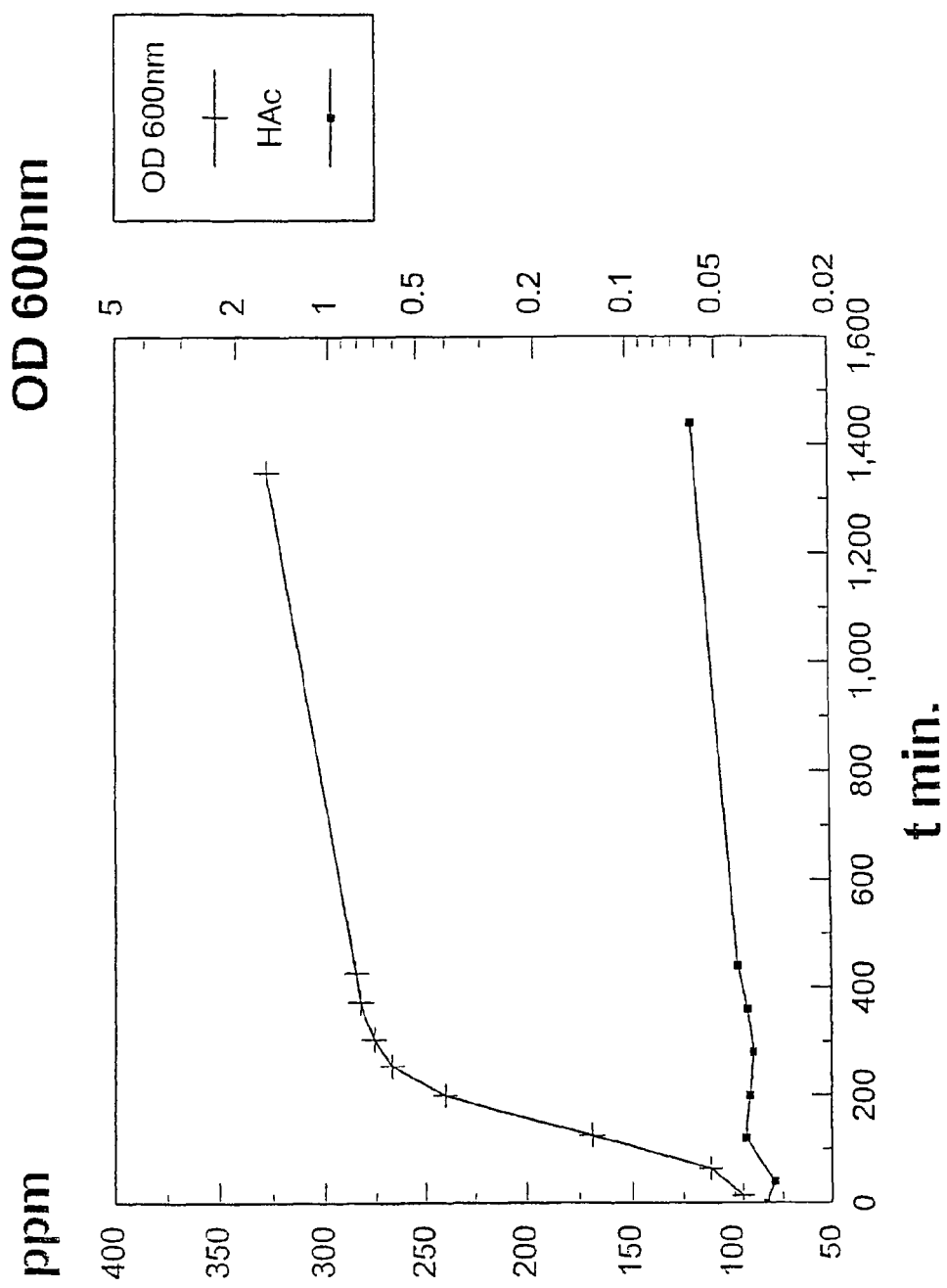
Figure 3F:
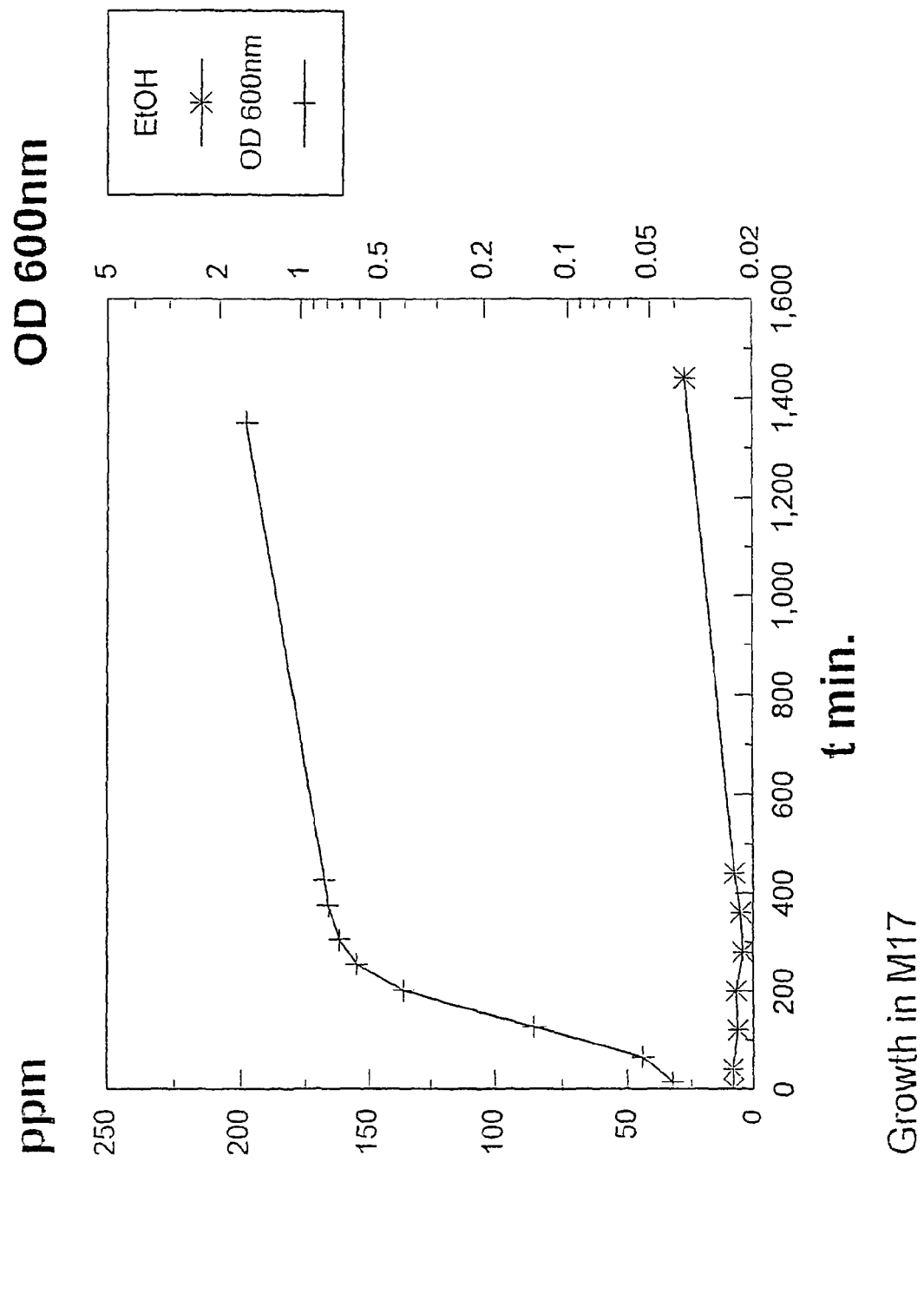

Terzaghi, Betty et al., "Improved medium for lactic streptococci and their bacteriophages.", *Applied Microbiology*, vol. 29, No. 6, pp. 807-813 (1975).

Westerfeld, W., "A colorimetric determination of blood acetoine.", *Journal of Biological Chemistry*, vol. 16, pp. 495-502 (1945).

Pascal, Marie-Claire et al., "Genetic analysis of mutants of *Escherichia coli* K12 and *Salmonella typhimurium* LT2 deficient in hydrogenase activity." Molec. Gen. Genet., vol. 141, pp. 173-179 (1975).

Pascal, Marie-Claire et al., "Mutants of *Escherichia coli* K12 with defects in anaerobic pyruvate metabolism" Journal of General Microbiology, vol. 124, pp. 35-42 (1980).

Varenne, S. et al., "A mutant of *Escherichia coli* deficient in pyruvate formate lyase.", Molec. Gen. Genet., vol. 141, pp. 181-184 (1975).

F. Mat-Jan et al., "Mutants of *Escherichia coli* Deficient in the Fermentative Lactate Dehydrogenase", Journal of Bacteriology, vol. 171, No. 1, p. 342-348, Jan. 1989.

Arnau, et al., "Cloning, Expression, and Characterization of the *Lactococcus lactis* pfl Gene, Encoding Pyruvate Formate-Lyase", *Journal of Bacteriology*, vol. 179, No. 18, pp. 5884-5891, Sep. 1997.

Boumerdassi, et al., "Isolation and Properties of *Lactococcus lactis* subsp. *lactis* biovar diacetylactis CNRZ 483 Mutant Producing Diacetyl and Acetoin from Glucose", *Applied and Environmental Microbiology*, vol. 63, No. 6, pp. 2293-2299, Jun. 1997.

Hols, et al., "Acetate Utilization in *Lactococcus lactis* Deficient in Lactate Dehydrogenase: a Rescue Pathway for Maintaining Redox Balance", *Journal of Bacteriology*, vol. 181, No. 17, pp. 5521-5526, Sep. 1999.

Hugenholtz, et al., Abstract Only, "Diacetyl production by different strains of *Lactococcus lactis* subsp. *lactis* var. *diacetylactis* and *Leuconostoc* sp..", *Applied Microbiology and Biotechnology*, vol. 38, No. 1, pp. 17-22, 1992.

Lopez, et al., Abstract Only, "Cofactor Engineering: a Novel Approach to Metabolic Engineering in *Lactococcus lactis* by Controlled Expression of NADH Oxidsae", *Journal of Bacteriology*, vol. 180, No. 15, pp. 3804-3808, Aug. 1998.

McKay, et al., "Altered Metabolism in a *Streptococcus lactis* C2 Mutant Deficient in Lactic Dehydrogenase", *Journal of Diary Science*, vol. 57, No. 2, pp. 181-186, 1974.

Monnet, et al., "Diacetyl and α-Acetolactate Overproduction by *Lactococcus lactis* subsp. *lactis* Biovar Diacetylactis Mutants That Are Deficient in α-Acetolactate Decarboxylase and Have a Low Lactate Dehydrogenase Activity", *Applied and Environmental Microbiology*, vol. 66, No. 12, pp. 5518-5520, Dec. 2000.

Neves, et al., "Catabolism of mannitol in *Lactococcus lactis* MG1363 and a mutant defective in lactate dehydrogenase", *Microbiology*, vol. 148, pp. 3467-3476, 2002.

Pedersen, et al., Abstract Only, "Bacteriophage resistance of a deltathyA mutant of *Lactococcus lactis* blocked in DNA replication", *Applied and Environmental Microbiology*, vol. 68(6), pp. 3010-3023, Jun. 2002.

Platteeuw, et al., "Metabolic Engineering of *Lactococcus lactis*: Influence of the Overproduction of α-Acetolactate Synthase in Strains Deficient in Lactate Dehydrogenase as a Function of Culture Conditions", *Applied and Environmental Microbiology*, vol. 61, No. 11, pp. 3967-3971, Nov. 1995.

Sybesma, et al., "Effects of Cultivation Conditions on Folate Production by Lactic Acid Bacteria", *Applied and Environmental Microbiology*, vol. 69, No. 8, pp. 4542-4548, Aug. 2003.

Sybesma, "Metabolic Engineering of Folate Production in Lactic Acid Bacteria", Thesis, Chapter 3, pp. 63, 64, 69, and 78, 2003.

Smart, et al., "Effect of Oxygen on Lactose Metabolism in Lactic Streptococci", *Applied and Environmental Microbiology*, vol. 53, No. 3, pp. 533-541, Mar. 1987.

Sallami, et al., Abstract Only, "Impact of autolytic, proteolytic, and nisin-producing adjunct cultures on biochemical and textural properties of cheddar cheese", *J. Dairy Sci.*, vol. 87(6), pp. 1585-1594, Jun. 2004.

Wang, et al., "A Deficiency in Aspartate Biosynthesis in *Lactococcus lactis* subsp. *lactis* C2 Causes Slow Milk Coagulation", *Applied and Environmental Microbiology*, vol. 64, No. 5, pp. 1673-1679, May 1998.

Wang, et al., "Cloning Sequencing, and Expression of the Pyruvate Carboxylase Gene in *Lactococcus lactis* subsp. *lactis* C2", *Applied and Environmental Microbiology*, vol. 66, No. 3, pp. 1223-1227, Mar. 2000.

UniProtKB Database Search for protein sequences for Organism: "*Lactococcus lactis* subsp. *lactis* (*Streptococcus lactis*) [1360] and strain:CHCC373" http://www.uniprot.org/uniprot/?query=organism:1360+strain:"CHCC373", 1 page, Mar. 8, 2011.

\* cited by examiner

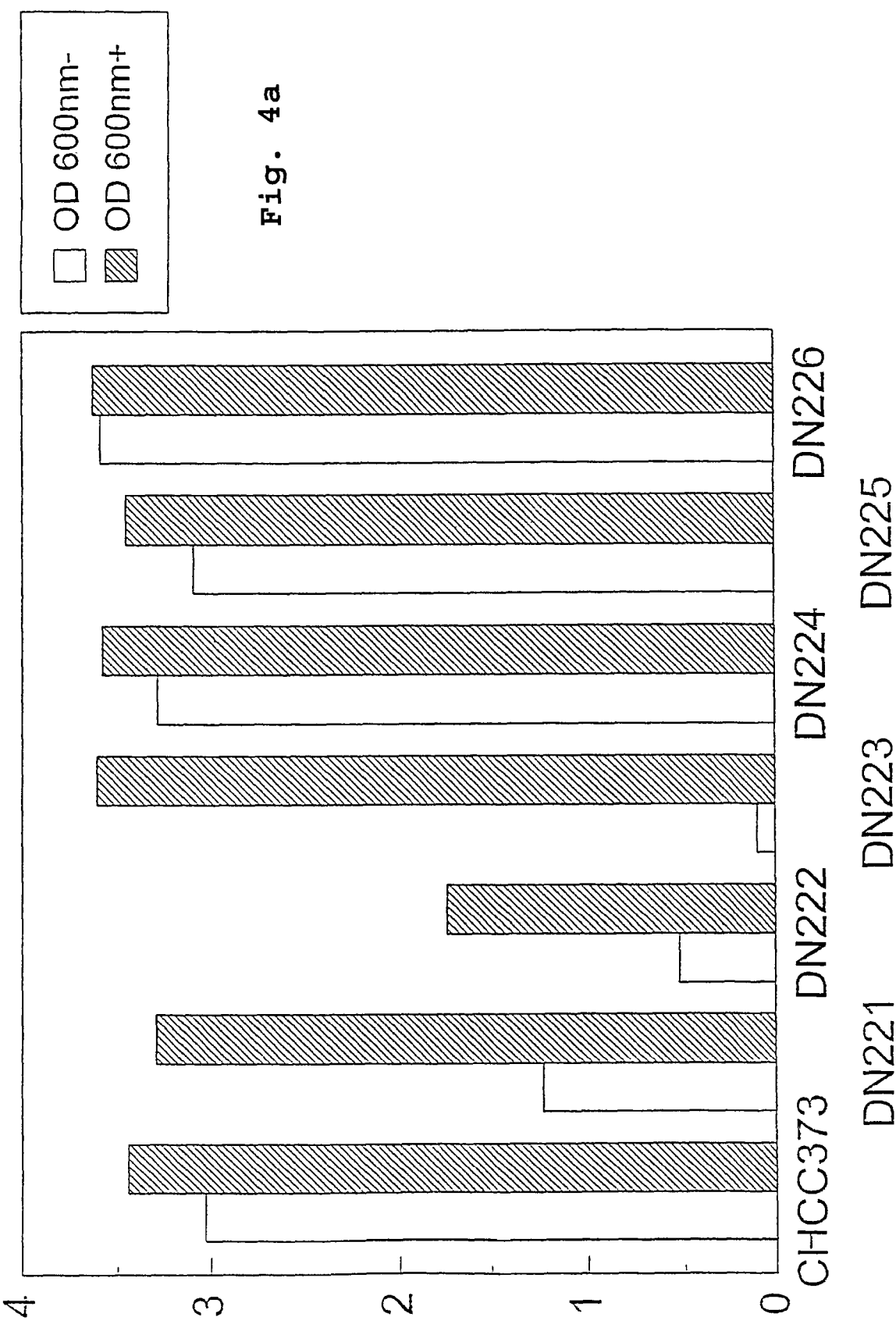

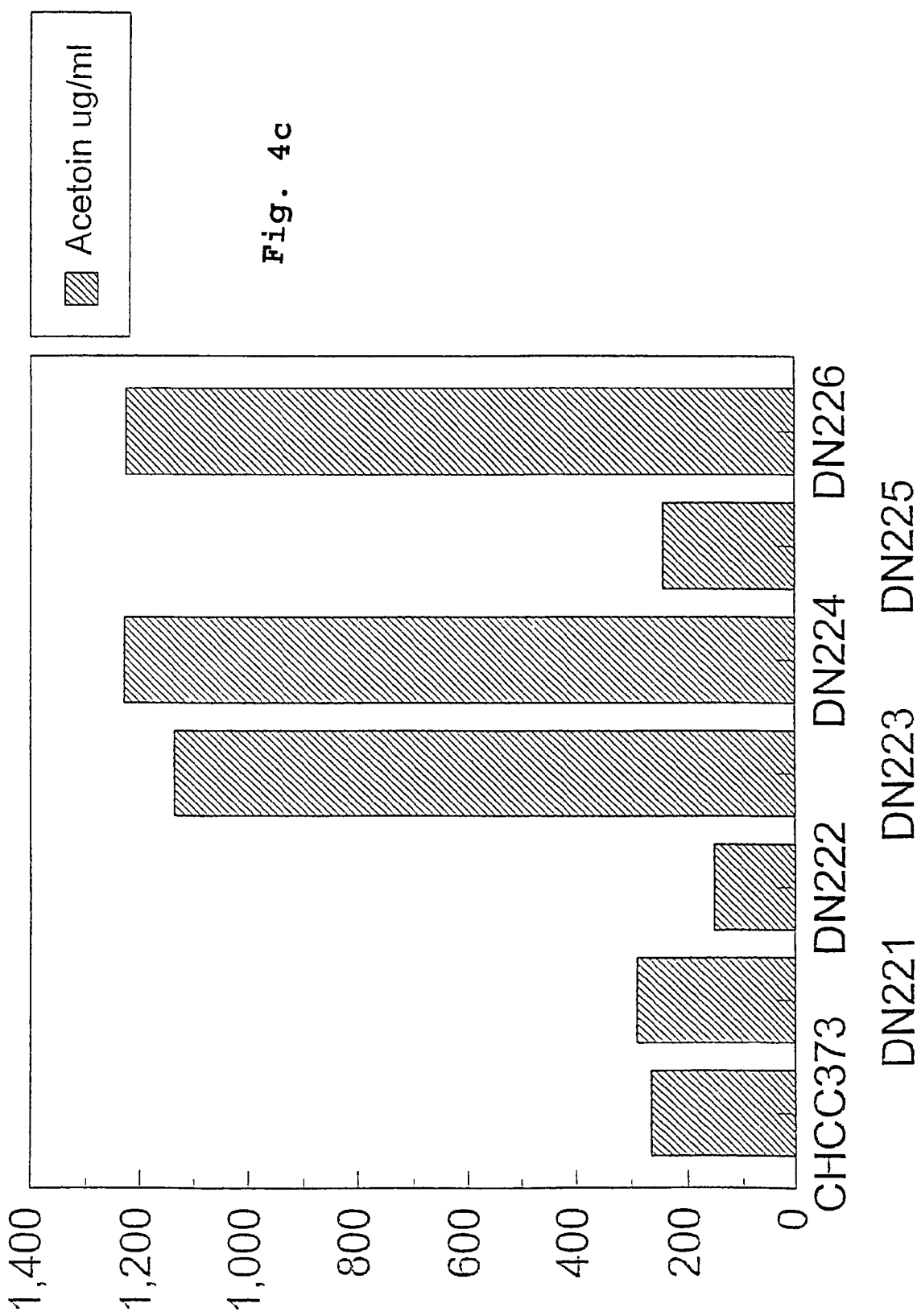

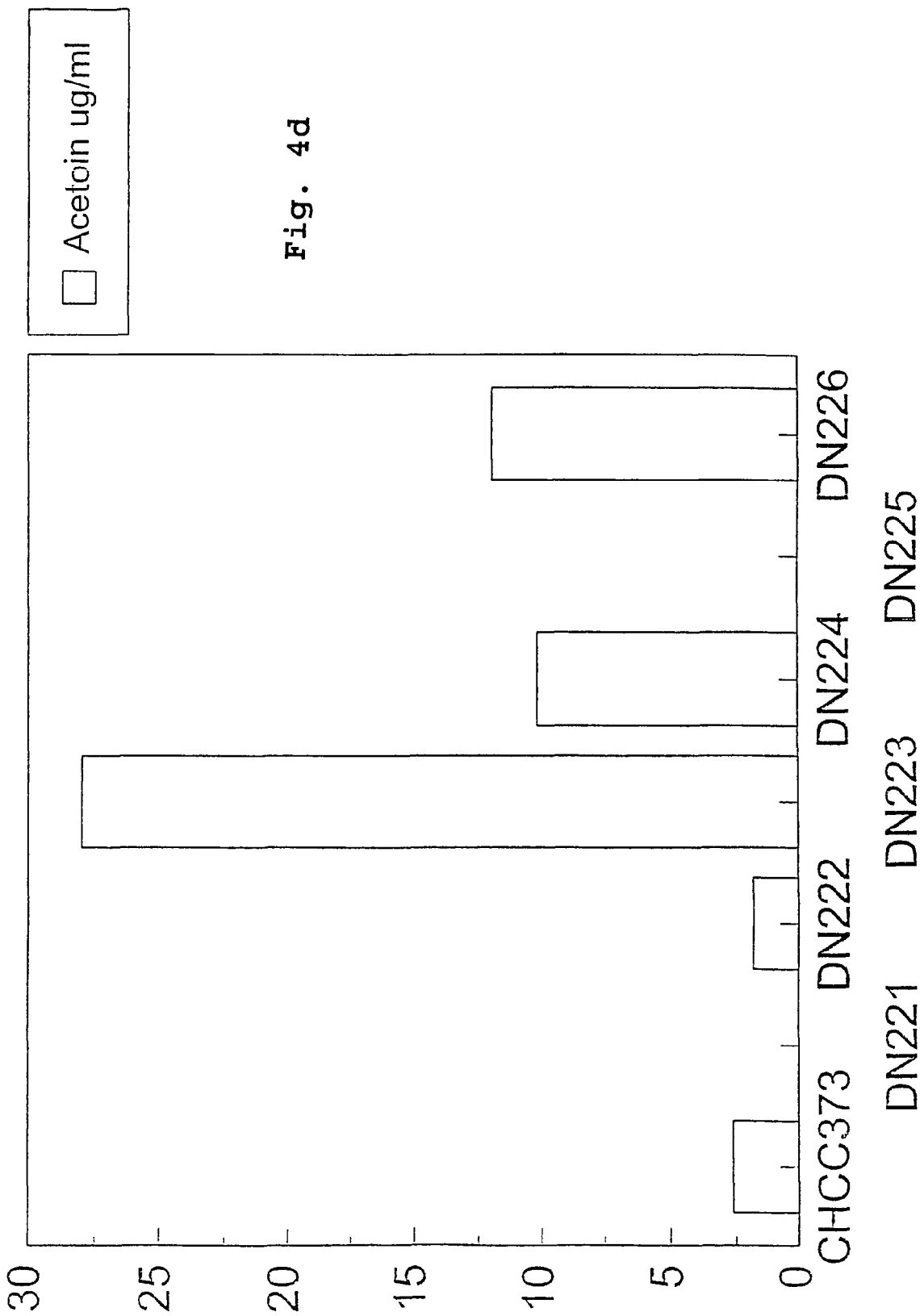

METABOLICALLY ENGINEERED LACTIC ACID BACTERIA AND THEIR USE

This is a division of Ser. No. 10/658,376, filed Sep. 10, 2003, now U.S. Pat. No. 7,465,575; which is a division of Ser. No. 08/981,098, filed Dec. 17, 1997, now U.S. Pat. No. 6,645, 754; which is a national stage of PCT/DK97/00335, filed Aug. 20, 1997; which is a continuation-in-part of Ser. No. 08/701,459 filed Aug. 22, 1996, now abandoned.

The prior application(s) set forth above are hereby incorporated by reference in their entirety.

CROSS-REFERENCE TO RELATED APPLICATIONS

Arnau, et al., PCT/DK97/00336, is related to metabolically engineered lactic acid bacteria and means for providing same. It is a continuation-in-part of Ser. No. 08/701,458, filed 22 Aug. 1996.

FIELD OF INVENTION

The present invention relates to the field of lactic acid bacterial starter cultures and in particular there is provided the means of metabolically engineering such bacteria to obtain mutants or variants hereof which, when they are used in the manufacturing of fermented food products produce increased amounts of desirable metabolites or reduced amounts of less desirable metabolites.

TECHNICAL BACKGROUND AND PRIOR ART

Lactic acid bacteria are used extensively as starter cultures in the food industry in the manufacture of fermented products including milk products such as e.g. yoghurt and cheese, meat products, bakery products, wine and vegetable products. *Lactococcus* species including *Lactococcus lactis* are among the most commonly used lactic acid bacteria in dairy starter cultures. However, several other lactic acid bacteria such as *Leuconostoc* species, *Pediococcus* species, *Lactobacillus* species and *Streptococcus* species. Species of *Bifidobacterium*, a group of strict anaerobic bacteria, are also commonly used in food starter cultures alone or in combination with lactic acid bacterial species.

When a lactic acid bacterial starter culture is added to milk or any other food product starting material under appropriate conditions, the bacteria grow rapidly with concomitant conversion of citrate, lactose or other sugar compounds into lactic acid/lactate and possibly other acids including acetate, resulting in a pH decrease. In addition, several other metabolites are produced during the growth of lactic acid bacteria. These metabolites include ethanol, formate, acetaldehyde, α-acetolactate, acetoin, diacetyl, and 2,3 butylene glycol (butanediol). Among these metabolites, diacetyl is an essential flavour compound which is formed during fermentation of the citrate-utilizing species of e.g. *Lactococcus, Leuconostoc* and *Lactobacillus*. Diacetyl is formed by an oxidative decarboxylation (FIG. 1) of α-acetolactate which is formed by the action of α-acetolactate synthetase (Als) from two molecules of pyruvate.

Pyruvate is a key intermediate of several lactic acid bacterial metabolic pathways including the citrate metabolism and the degradation of lactose or glucose to lactate. The pool of pyruvate in the cells is critical for the flux through the metabolic pathway leading to diacetyl, acetoin and 2,3 butylene glycol (butanediol) via the intermediate compound α-acetolactate due to the low affinity of α-acetolactate synthetase for pyruvate.

Pyruvate is converted to formate and acetyl coenzyme A (acetyl CoA) (FIG. 1) by the action of pyruvate formate-lyase (Pfl). This conversion takes place only under anaerobic conditions (Frey et al. 1994). Pfl is inactivated even at low levels of oxygen, and a switch from anaerobic to aerobic conditions will lead to significant changes in metabolic end product profiles in lactic acid bacteria with complete disappearance of ethanol and formate (Hugenholtz, 1993). Another factor which regulates the activity of Pfl is the pH. The pH optimum of Pfl is about 7 (Hugenholtz, 1993).

An alternative pathway for the formation of acetyl CoA from pyruvate (FIG. 1) in a lactic acid bacterium is by the activity of the pyruvate dehydrogenase complex (PDC). In contrast to Pfl, PDC has a very low activity under anaerobic conditions due to the inhibitory effect of NADH on that enzyme (Snoep et al. 1992). This enzyme requires the presence of lipoic acid as a co-factor to be active.

Additionally, acetyl CoA can be produced in lactic acid bacteria from acetate under aerobic as well as under anaerobic conditions.

Accordingly, it is conceivable that the pyruvate pool is increased under anaerobic conditions if the lactic acid bacterial strain is defective in enzyme systems involved in pyruvate consumption, including Pfl. As mentioned above, an increased pyruvate pool may lead to an increased flux from pyruvate towards acetoin and diacetyl or other metabolites derived from α-acetolactate. Thus, it is to be expected that fermented food products which are produced by using a lactic acid bacterial starter culture having a reduced Pfl activity or completely lacking such activity contain an increased amount of acetoin or other of the above metabolites. Conversely, the such starter cultures may produce reduced amounts of other metabolites, including ethanol and acetate and possibly, acetaldehyde.

Recent studies have shown that when *L. lactis* is lacking the lactate dehydrogenase (Ldh) which is involved in the major pyruvate consuming pathway leading to lactate, more pyruvate is directed towards acetoin and butanediol via α-acetolactate, possibly resulting in increased formation of the intermediate product diacetyl (Platteeuw et al., 1995; Gasson et al., 1996).

Overproduction of α-acetolactate synthetase in *Lactococcus lactis* as another approach of metabolically engineering lactic acid bacteria to produce increased amounts of diacetyl has been disclosed by Platteeuw et al. 1995.

The potential of using *L. lactis* strains with reduced pyruvate formate-lyase activity as a means of increasing diacetyl formation is mentioned by Hugenholtz, 1993. It is suggested by this author that the combination of three strategies: 1) Ldh inactivation by mutation/genetic engineering, 2) Pfl inactivation by aeration and/or low pH and 3) acetolactate decarboxylase (ALD) inactivation by mutation/genetic engineering could result in a high production of α-acetolactate from lactose.

However, the suggested inactivation of Pfl activity by aeration and/or low pH is not feasible or possible in the industrial production of lactic acid bacterially fermented dairy products or other fermented food products, as the production hereof generally takes place under essentially anaerobic conditions. Furthermore, the pH of the starting materials including milk is typically about 7 and it is generally not desirable to lower the pH of the food material to be fermented.

Whereas it has been suggested to modify the Pfl activity of lactic acid bacteria as a means of changing their production of metabolites in a desirable direction by manipulating the growth conditions, there have been no suggestions in the prior art to utilize metabolically engineered lactic acid bacteria which have a modified Pfl activity under industrially appropriate and feasible culturing conditions.

A method that allows isolation of mutants of gram-negative bacteria devoid of Pfl activity has been disclosed by Pascal et al., 1974. This method includes the selection of Pfl defective mutants of *E. coli* and *Salmonella typhimurium* based on their lack of ability to generate $H_2$ and $CO_2$ in the absence of formate, when they are incubated under anaerobic condition in media containing glucose or pyruvate. However, such a selection method cannot be used for selection of Pfl defective mutants of lactic acid bacteria, since these organisms lack the enzyme that catalyses production of $H_2$ and $CO_2$ from formate.

Accordingly, the prior art does not contain any guidance with respect to designing a feasible method of isolating a lactic acid bacterial Pfl detective (Pfl⁻) mutant.

Experiments performed by the inventor with the minimal medium BA (Clark and Maaløe, 1967) for *E. coli*, showed that this medium did not support the aerobic growth of lactic acid bacteria. However, if cultivated in this medium together with *E. coli* the growth of lactic acid bacteria was supported, indicating that *E. coli* produces a factor needed for the growth of the lactic acid bacteria. It has later been found that this growth factor is acetate, which led to the development of the DN-medium (Dickely et al., 1995).

It has now surprisingly been found that wild-type strains of lactic acid bacteria such as strains of *Lactococcus* and *Streptococcus* including as examples *Lactococcus lactis* and *Streptococcus thermophilus* strains under anaerobic conditions grow well on the DN-medium (Dickely et al., 1995) in the absence of acetate. These unexpected findings have made it possible to develop a novel and simple method for the isolation of Pfl defective lactic acid bacterial mutants based on the finding that such mutants, in contrast to the phenotypically Pfl⁺ wild-type strains, are unable to grow under anaerobic conditions on DN-medium in the absence of acetate.

Additionally, having such a method allowing the selection of Pfl defective lactic acid bacterial mutants at hand has made it possible to provide further mutated cells which in addition to being Pfl⁻ are mutated in one or more genes involved in the citrate/sugar metabolic pathways such as e.g. the ldh gene coding for lactate dehydrogenase (Ldh) so as to provide a variety of metabolically engineered lactic acid bacteria having highly desirable improved characteristics with respect to metabolite (fermentation end product) production.

The above findings have thus opened up for a novel approach for providing useful metabolically engineered lactic acid bacterial starter cultures which approach is based on relatively simple classical random mutagenesis methods or the selection of spontaneously occurring mutants and which does not involve in vitro genetic engineering. From a practical technological point of view this is advantageous, since in most countries the use of genetically engineered food starter cultures is still conditional on approval by regulatory bodies.

SUMMARY OF THE INVENTION

Accordingly, the invention provides in a first aspect a method of isolating a pyruvate formate-lyase (Pfl) defective lactic acid bacterium, the method comprising the steps of
(i) providing a wild-type lactic acid bacterial strain which under aerobic conditions is not capable of growth in the absence of acetate in a medium not containing lipoic acid, but which is capable of growth is such medium under anaerobic conditions, and
(ii) selecting from said wild-type strain a mutant which under said conditions essentially does not grow in the absence of acetate.

In a further aspect, the invention relates to a Pfl defective mutant lactic acid bacterium which is obtainable by the above method and having, relative to the wild-type strain from which it is derived, at least one of the following characteristics:
(i) essentially the same growth rate when cultivated under aerobic conditions in M17 medium,
(ii) a reduced growth rate or a reduced rate of acid production when cultivated under anaerobic conditions in M17 medium or in reconstituted skim milk (RSM),
(iii) essentially no production of formate under the anaerobic conditions of (ii),
(iv) a reduced production of ethanol or acetate under said above anaerobic conditions, and/or
(vi) an increased production of at least one α-acetolactate-derived metabolite when cultivated under anaerobic conditions in RSM.

In a still further aspect, there is provided a method of isolating a Pfl and lactate dehydrogenase (Ldh) defective lactic acid bacterium which is not capable of growth under anaerobic conditions in the presence of acetate, said method comprising
initially selecting a Pfl defective lactic acid bacterium in accordance with the above method, and
(ii) selecting from said Pfl defective lactic acid bacterium a strain which is incapable of growing under anaerobic condition in an acetate-containing medium.

The invention pertains in another aspect to a Pfl and Ldh defective mutant lactic acid bacterium which is not capable of growing under anaerobic conditions in the presence of acetate, said bacterium being obtainable by the above method of isolating a Pfl and lactate dehydrogenase (Ldh) defective lactic acid bacterium, and having, relative to a wild-type lactic acid bacterium or its Pfl defective parent strain, at least one of the following characteristics:
(i) essentially the same growth yield when cultivated under aerobic conditions in M17 medium,
(ii) a reduced capability of converting lactose to lactate,
(iii) an increased production of α-acetolactate, and/or
(iv) an increased production of an α-acetolactate derived metabolite.

In further aspects, the invention relates to a mutant or variant of the above Pfl and Ldh defective mutant which mutant or variant is capable of growing anaerobically, to a method of producing a food product, comprising adding to the food product starting materials a culture of any of the above mentioned lactic acid bacteria and a method of producing a lactic acid bacterial metabolite, comprising cultivating any of the above mentioned lactic acid bacteria under conditions where the metabolite is produced, and isolating the metabolite from the culture.

There is also provided a lactic acid bacterial starter culture composition comprising any of the above mentioned lactic acid bacteria.

DETAILED DISCLOSURE OF THE INVENTION

The present invention provides in a first aspect a method of isolating a pyruvate formate-lyase (Pfl) defective mutant lactic acid bacterium. As used herein the expression "pyruvate formate-lyase defective" indicates that the lactic acid bacterial mutant as compared to the wild-type parent strain has a reduced Pfl activity or that the Pfl activity is absent irrespective of the growth conditions, Pfl activity being expressed herein in terms of formate production. Such a mutant strain is also referred to herein as a strain having a Pfl⁻ phenotype.

As used herein, the expression "lactic acid bacterium" designates gram positive, microaerophilic or anaerobic bacteria which ferment sugar with the production of acids including lactic acid as the predominantly produced acid, acetic acid, formic acid and propionic acid. The industrially most useful lactic acid bacteria are found among *Lactococcus* species, *Streptococcus* species, *Lactobacillus* species, *Leuconostoc* species, *Pediococcus* species and *Brevibacterium* species. Also the strict anaerobes belonging to the genus *Bifidobacterium* is generally included in the group of lactic acid bacteria.

A lactic acid bacterial mutant as defined above can be derived by selecting a spontaneously occurring mutant of a wild-type strain of a lactic acid bacterium which has the characteristic that it, when it is cultivated under aerobic conditions in a medium which does not contain lipoic acid, has a growth requirement for acetate, but which under anaerobic conditions is capable of growing in such a medium in the absence of acetate. Alternatively, the mutant of the wild-type lactic acid bacterial strain can be provided by subjecting the strain to a mutagenization treatment prior to the selection of a mutant having the above characteristics of the Pfl defective strain.

It is assumed that these different requirements for acetate under the above aerobic and anaerobic conditions, respectively is caused by the facts that under aerobic conditions insufficient amounts of acetyl CoA is formed by the lactic acid bacterium due to at least two circumstances: (i) in the absence of lipoic acid, an essential co-factor for the activity of the acetyl CoA generating pyruvate dehydrogenase complex (PDC), this enzyme complex does not generate acetyl CoA and (ii) the other major acetyl CoA generating enzyme, pyruvate formate-lyase (Pfl) is inactivated in the presence of oxygen. Therefore, under such aerobic conditions, the wild-type lactic acid bacterium requires acetate as an alternative source of acetyl CoA. In contrast, under anaerobic conditions, the Pfl is activated and assumingly provides acetyl CoA in sufficient amounts for growth of the bacterium. As it is mentioned above, these observations were the starting point for designing the present method of isolating a Pfl defective mutant of a lactic acid bacterium as described herein and the use hereof as an intermediate for providing further modified strains of lactic acid bacteria.

In accordance with one embodiment of the invention, this method provides in a first step the provision of a wild-type lactic acid bacterium having the above acetate requirement characteristics, followed by subjecting the bacterium to a mutagenization treatment. In accordance with the invention, suitable mutagens include conventional chemical mutagens and UV light. Thus, as examples, a chemical mutagen can be selected from (i) a mutagen that associates with or become incorporated into DNA such as a base analogue, e.g. 2-aminopurine or an interchelating agent such as ICR-191, (ii) a mutagen that react with the DNA including alkylating agents such as nitrosoguanidine or hydroxylamine, or ethane methyl sulphonate (EMS).

Although the lactic acid bacterial mutant can be provided by subjecting a parent strain to a chemical mutagenization treatment followed by selecting a Pfl⁻ mutant, it will be understood that it would also be possible to provide the mutant by selecting a spontaneously occurring mutant in accordance with the selection procedure as described herein.

As an alternative to one presently preferred method of providing the mutant by random mutagenesis, it is also possible to provide such a mutant by site-directed mutagenesis, e.g. by using appropriately designed PCR techniques or by using a transposable element which is integratable in lactic acid bacterial replicons.

When a mutagenization step is included, the mutagenized strain is, subsequent to the mutagenization treatment, cultivated under anaerobic conditions in a defined medium not containing lipoic acid in the absence or presence, respectively of acetate, and a mutant strain, which in contrast to the wild-type parent strain essentially does not grow under these conditions in the absence of acetate, is selected. It is assumed that such a mutant strain has a defect in the gene coding for the Pfl polypeptide implying that the production of the enzyme is at least partially blocked or that the enzyme is produced in an at least partially inactive form. This assumption can be affirmed by testing the selected mutant for lack of production of formate or alternatively, a reduced pyruvate formate-lyase activity.

When the mutant is provided as a spontaneously occurring mutant the above wild-type strain is subjected to the selection step without any preceding mutagenization treatment. The lactic acid bacterial wild-type parent strain can be selected from any industrially suitable lactic acid bacterial species, i.e. the strain can be selected from the group consisting of a *Lactococcus* species, a *Lactobacillus* species, a *Leuconostoc* species, a *Pediococcus* species, a *Streptococcus* species and a *Bifidobacterium* species In particular useful embodiments, the lactic acid bacterium is a *Lactococcus* lactis or a *Streptococcus thermophilus*. Examples of presently preferred lactic acid bacteria are *Lactococcus lactis* subspecies *lactis* and *Lactococcus lactis* subspecies *lactis* biovar *diacetylactis*.

A Pfl defective (Pfl⁻ phenotype) mutant lactic acid bacterium which can be obtained by the above method has, relative to the wild-type parent strain one or more phenotypically recognizable characteristics distinguishing it from the parent strain. Thus, the Pfl⁻ mutant strain may have essentially the same growth rate when cultivated under aerobic conditions in M17 medium but a reduced growth rate or a reduced acid production when cultivated under anaerobic conditions in conventional media such as the M17 medium or reconstituted skim milk (RSM), essentially no production of formate, a reduced production of ethanol or acetate under said above anaerobic conditions and/or an increased production of at least one α-acetolactate-derived metabolite when cultivated under anaerobic conditions, e.g. in RSM.

Several of these characteristics may be desirable for specific purposes. In the production of a food product it may thus be advantageous that the strain produces lesser amounts of acids, formate, acetate or ethanol, whereas an enhanced production of α-acetolactate derived aroma or flavour compounds can be highly desirable, in particular in the production of dairy products. Such desirable compounds include acetoin, diacetyl and 2,3 butylene glycol. In useful embodiments, the production of such metabolites such as acetoin is increased by at least 50%, more preferably by at least 100% and in particular by at least 200%. Besides being useful in the manufacturing of a food product, a mutant strain overproducing α-acetolactate derived metabolites can also be used in the production of the metabolites as such.

In accordance with the invention, a Pfl defective (Pfl⁻) mutant strain is selected from a *Lactococcus* species, a *Lactobacillus* species, a *Leuconostoc* species, a *Pediococcus* species, a *Streptococcus* species and a *Bifidobacterium* species. In this context, one preferred species is *Lactococcus* lactis including *Lactococcus lactis* subspecies *lactis* and *Lactococ-* cus lactis subspecies lactis biovar diacetylactis, e.g. the Lactococcus lactis subspecies lactis strain DN221 which has been deposited under the accession No. DSM 11034, or a Lactococcus lactis strain having essentially the characteristics of that strain, or the Lactococcus lactis subspecies lactis biovar diacetylactis strain DN227 which has been deposited under the accession No. 11040, or a Lactococcus lactis strain having essentially the characteristics of that strain.

It will be understood that the Plf defective lactic acid bacterial mutant can be utilized as a host for the cloning of a pfl gene by complementation of the defective gene.

Importantly, the Plf⁻ strain can also be used as a parent strain for isolating mutants having further useful enzymatic defects as it will be described in the following.

Lactate dehydrogenase (Ldh) is, as it can be seen from FIG. 1, another enzyme which in lactic acid bacteria contribute to the consumption of the pyruvate pool, the activity of the enzyme predominantly resulting in the production of lactate. It was contemplated that the metabolic flux towards α-acetolactate and metabolites derived from this intermediate could be further increased by providing a mutant strain which in addition to having a defect in the Pfl activity is defective in Ldh.

Therefore, a strategy for isolating and selecting a lactic acid bacterium which in addition to being Pfl defective is also Ldh defective (Ldh⁻), i.e. having the Pfl⁻ Ldh⁻ phenotypes, was developed based on the following considerations: During anaerobic growth of wild-type lactic acid bacteria the NADH being produced in the glycolysis is converted to NAD⁺ during production of lactate and to some extent during the production of ethanol. Accordingly, it was hypothesized that a double mutant having the Pfl⁻ Ldh⁻ phenotype would be unable to grow under anaerobic conditions, i.e. such a strain would have the additional phenotype Ang⁻ (inability to grow anaerobically). This hypothesis was based on the assumption that such a double mutant would be unable to regenerate NAD⁺ from NADH under anaerobic conditions, since Pfl would be blocked by a mutation (whereas under aerobic conditions, NADH can be converted to NAD⁺ by NADH oxidase), PDC would be blocked due to inhibition by NADH and Ldh would be blocked by mutation. It was thus contemplated that a Pfl⁻ Ldh⁻ double mutant could grow under aerobic conditions but not under anaerobic conditions.

Based on the above considerations, a method of isolating a Pfl and lactate dehydrogenase (Ldh) defective lactic acid bacterium which is not capable of growth under anaerobic conditions in the presence of acetate, i.e. a Pfl⁻ Ldh⁻Ang⁻ phenotype, was developed. The method comprises as a first step, the selection of a Pfl defective lactic acid bacterium in accordance with the above method, followed by selecting from this Pfl defective bacterium a strain which is incapable of growing under anaerobic conditions in an acetate-containing medium.

In one presently preferred embodiment this method includes the step of subjecting, prior to selection of a strain which is incapable of growing under anaerobic conditions in an acetate-containing medium, the Pfl defective lactic acid bacterium to a mutagenization treatment and subsequently selecting a mutant which under said conditions essentially does not grow under said anaerobic conditions.

The above method of isolating the Plf and Ldh defective mutant results in a strain having an Ldh specific activity which is reduced relative to that of its parent (Pfl defective) strain. Preferably, the thus selected mutant has an Ldh specific activity which is less than 10 units/mg protein of a cell free extract of the bacterium.

Typically, the thus reduced Ldh specific activity corresponds to at the most 50% activity relative to the wild-type or Pfl⁻ parent strain, such as at the most 25% or preferably, at the most 10% activity such as at the most 5% relative to the parent strains. It is particularly preferred that the mutant strain essentially is devoid of Ldh activity.

The mutagenization step whereby the Pfl⁻ Ldh⁻ Ang⁻ mutant is produced from the Pfl⁻ mutant can be performed according to the methods as described above for the mutagenization of the wild-type strain. It follows from the above description of this initial step of providing the Pfl⁻ mutant that useful strains can be selected from the group consisting of a Lactococcus species, a Lactobacillus species, a Leuconostoc species, a Pediococcus species, a Streptococcus species and a Bifidobacterium species. A presently preferred lactic acid bacterium is Lactococcus lactis including Lactococcus lactis subspecies lactis and Lactococcus lactis subspecies lactis biovar diacetylactis.

In accordance with the invention there is also provided a Pfl and Ldh defective mutant lactic acid bacterium which is obtainable by the above method. In addition to its Pfl⁻ Ldh⁻ Ang⁻ phenotypes, such a mutant strain can be distinguished from a wild-type lactic acid bacterium or its Pfl defective parent strain in one or more further characteristics. Thus, the mutant strain may have essentially the same growth yield when cultivated under aerobic conditions in M17 medium, a reduced capability of converting lactose to lactic acid/lactate, increased production of α-acetolactate and/or an increased production of an α-acetolactate derived metabolite. Surprisingly, the production of α-acetolactate and/or metabolites derived from α-acetolactate was not only increased under aerobic conditions where the mutant strain can grow, but also under anaerobic conditions where essentially no growth occurred.

As it is shown in the below Examples, the increase of production of α-acetolactate and metabolites derived therefrom was of a significant magnitude. Thus, Pfl⁻ Ldh⁻ Ang⁻ mutants according to the invention preferably have a production of aacetolactate and/or metabolites derived therefrom which, relative to a wild-type strain of the same species, is increased by at least 50%, such as by at least 100%. It is even more preferred the production is increased by at least 200% such as at least 1000%.

In accordance with the invention, the Pfl⁻ Ldh⁻ Ang⁻ mutant can be of any lactic acid bacterial species selected from a Lactococcus species, a Lactobacillus species, a Leuconostoc species, a Pediococcus species, a Streptococcus species and a Bifidobacterium species. One preferred species is Lactococcus lactis including Lactococcus lactis subspecies lactis such as the strain designated DN223 which is described in the following and which is deposited under the accession No. DSM 11036 or a Lactococcus lactis strain having essentially the characteristics of that strain, and Lactococcus lactis subspecies lactis biovar diacetylactis.

As a result of the enzyme defects of the present Pfl⁻ Ldh⁻ Ang⁻ lactic acid bacterial mutant, such a mutant is capable of converting a substantial proportion of the intracellular pyruvate pool to α-acetolactate and further to one or more of the metabolites which can be formed from this intermediate compound, including acetoin, butanediol and/or diacetyl which latter compound can be formed by chemically oxidizing α-acetolactate. Thus, in one preferred embodiment, the Pfl⁻ Ldh⁻ Ang⁻ mutant is capable of converting at least 15% of pyruvate being catabolized to acetoin, more preferably at least 30%. In even more preferred embodiments, this conversion is at least 40%, such as at least 50% or even at least 60%.

In a further aspect, the invention relates to a mutant or variant of the above Pfl⁻ Ldh⁻ Ang⁻ mutant lactic acid bacterium which is capable of growing anaerobically. Such a mutant or variant strain can be provided by selecting a spontaneous mutant of the above mutant bacterium, which mutant or variant strain can grow anaerobically. Alternatively, the mutant or variant strain can be made by subjecting the Pfl⁻ Ldh⁻ Ang⁻ mutant to a further mutagenization treatment in accordance with a method as described above, and selecting a strain being capable of growing anaerobically. It is contemplated that such mutants or variants would have regained the ability to convert NADH to NAD⁺ under anaerobic conditions, either by mutations in systems secondary to Ldh or Pfl, or by reversion of the Pfl⁻ phenotype to Pfl⁺ phenotype. In wild-type lactic acid bacteria, the level of NADH is high and it can be oxidized via lactate and/or ethanol production, i.e. via the pyruvate metabolism. The implication hereof is that lactic acid bacteria produce relatively high levels of lactate and/or ethanol as compared to aerobic conditions. From this it also follows that the metabolites having an aroma effect (diacetyl, acetoin) are only produced at relatively low levels.

It was found that this general picture was still found in the present Ang⁺ mutant or variant of the Pfl⁻ Ldh⁻ Ang⁻ mutant. However, it was surprisingly found that such a mutant/variant has, relative to its parent strain and to the wild-type strain, a significantly altered production of aroma compounds under anaerobic growth conditions. Thus, the above Ang⁺ mutant/variant may be one which has a production of acetaldehyde which relative to the original wild-type strain is increased at least 2-fold, such as at least 5-fold or even at least 8-fold. The mutant variant may also have a production of the diacetyl precursor α-acetolactate which, also relative to the wild-type strain is increased at least 5-fold such as at least 10-fold.

Also, the production of acetoin and/or formate may be significantly increased in such a mutant/variant. Thus, as one typical example, the mutant/variant is one which, when grown anaerobically in reconstituted skim milk powder, produces in excess of 1 mM acetoin and/or in excess of 10 mM formate.

A mutant or variant having the latter characteristic is assumingly Ldh defective but has the wild-type Pfl activity, i.e. it has the phenotype Pfl⁺ Ldh⁻ Ang⁺. One example of such a strain is the *Lactococcus lactis* subspecies *lactis* DN224 deposited under the accession No. DSM 11037 or a *Lactococcus lactis* strain having essentially the characteristics of that strain. Another example of the present mutant or variant is a strain which is Pfl defective and has the wild-type Ldh activity, i.e. having the phenotype Pfl⁻ Ldh⁺ Ang⁺.

In addition to being a starting material for providing further lactic acid bacterial mutants or variants, the above Pfl⁻ Ldh⁻ Ang⁻ mutant can be utilized as host for cloning of genes which can restore the ability of the mutant to grow under anaerobic conditions.

Such a mutant can also, as it is described above by way of example, be used for selecting further mutants having regained the capability of growing anaerobically e.g. due to mutations whereby an increased amount of one or more NADH oxidoreductases is produced. Such oxidoreductases include diacetyl reductase (Dr) and Ldh.

The mutant can also be one in which the mutation results in overproduction and/or enhanced activity of an enzyme, the activity of which can be limiting for a pathway in which a NADH dependent oxidoreductase is involved. Such an overproduction or enhanced activity can e.g. be of the α-acetolactate synthetase (Als), the increased production or activity of which would in turn result in an increased production of substrate for diacetyl reductase. Alternatively, the mutation may result in the above enzyme having an increased activity.

NADH dependent oxidoreductases require a substrate. Thus, as an example, acetoin is the substrate for the oxidoreductase diacetyl reductase (see FIG. 1). Accordingly, it is contemplated that the above Pfl⁻ Ldh⁻ Ang⁻ mutant can be used for selecting a mutant which does not grow, even if the oxidoreductase substrate such as acetoin is added to the medium. Such a mutant assumingly will have a defect in one or more of its oxidoreductases e.g. diacetyl reductase.

Any of the above mutants or variants are potentially useful in the production of food products and accordingly, the invention relates in a further aspect to a method of producing a food product which method comprises that a culture of a lactic acid bacterium as described herein is added to the food product starting materials which are then kept under conditions appropriate for the bacteria to grow and/or to be metabolically active. The purpose of the addition of the lactic acid bacteria depends of the food product. In some instances, a lactic acid bacterium according to invention is used to provide an increased production in the food product, such as e.g. a dairy product, of a particularly desirable aroma compound, such as diacetyl, acetoin or acetaldehyde. Other examples of food products where use of the present mutant strains is contemplated include meat products, vegetables, bakery products and wine.

It will also be understood that the presently provided strains will be highly useful as production strains in the manufacturing of lactic acid bacterial metabolite compounds including the above aroma compounds. Accordingly, the invention encompasses in a still further aspect a method of producing a lactic acid bacterial metabolite. Such a method comprises cultivating one or more of the lactic acid bacteria as disclosed herein in a suitable medium under industrially feasible conditions where the metabolite is produced, and isolating, if required, the metabolite from the culture. The metabolite can be isolated in accordance with any suitable conventional method of isolating the particular compound(s) from the cultivation medium. It is also possible to use the cultivation medium containing the outgrown culture of lactic acid bacteria directly as a source of one or more metabolites.

A specific example of such a production method for a lactic acid bacterial metabolite is a method of producing what is normally referred to in the art as "starter distillate" which is a diacetyl-containing flavouring product conventionally made by cultivating a conventional wild-type starter culture strain of a lactic acid bacterium which produces acetoin and/or diacetyl in a suitable medium and isolating the metabolites by distillation to provide a concentrate of the metabolites. This product is used for flavouring of butter, margarine, spreads, cereal products and pop-corn. It has been found that by using the strains DN223 or DN224, such a starter distillate can be obtained that has a content of diacetyl which, in comparison with a conventional starter distillate, is at least 2-fold.

It is convenient to provide the lactic acid bacterium according to the invention, both when it is used as a food production strain and as a production strain for metabolites, as a lactic acid bacterial starter culture composition comprising the lactic acid bacterium selected for the specific use. Typically, such compositions contain the bacterium in concentrated form e.g. at a concentration of viable cells (colony forming units, CFUS) which is in the range of $10^5$ to $10^{13}$ per g of the composition such as a range of $10^6$ to $10^{12}$ per g. Additionally, the starter culture composition may contain further components such as bacterial nutrients, cryoprotectants or other substances enhancing the viability of the bacterial active ingredient during storage. The composition can be in the form of a frozen or freeze-dried composition.

Figure 4B:
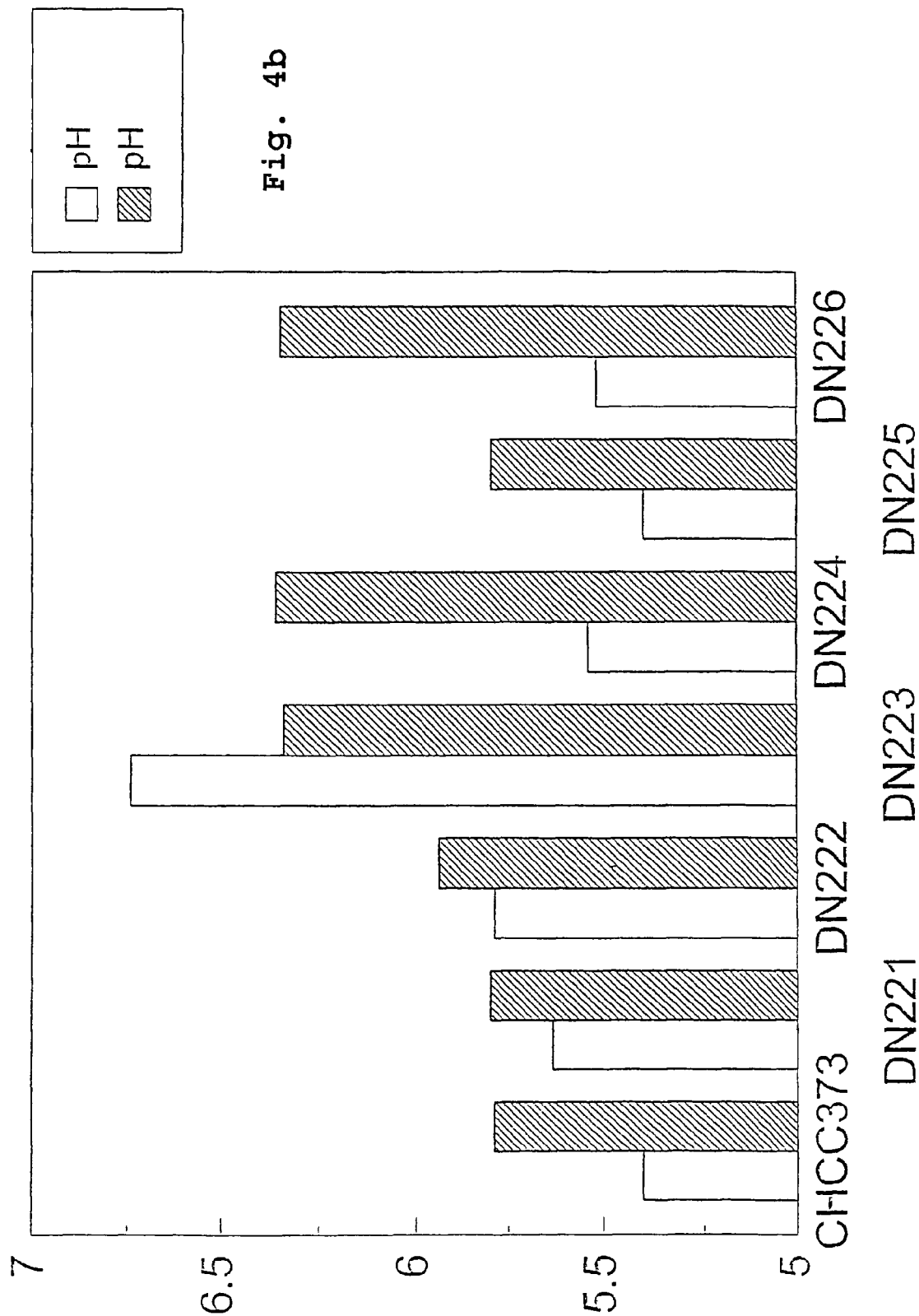

The invention is further illustrated in the following examples and the drawings wherein:

FIG. 1 illustrates the pyruvate metabolism in Lactic acid bacteria; the shown enzymatic pathways are: PFL, pyruvate formate-lyase; PDC, pyruvate dehydrogenase complex; LDH, lactate dehydrogenase; ALS, acetolactate synthetase; ILVB, second acetolactate synthetase; ALD, acetolactate decarboxylase; DR, diacetyl reductase, FIG. 2 illustrates pH, production of formate (HCOOH), acetate (HAc) and ethanol (EtOH) for *Lactococcus lactis* subspecies *lactis* CHCC373 and the mutant DN221 derived therefrom when these strains are cultivated under anaerobic conditions in reconstituted skim milk (RSM), FIG. 3 illustrates $OD_{600}$, production of formate (HFo), acetate (HAc) and ethanol (EtOH) for *Lactococcus lactis* sub-species *lactis* CHCC373 and the mutant DN221 derived therefrom when these strains are cultivated under anaerobic conditions in M17 medium, and FIG. 4 shows the growth, acidification and acetoin production of *Lactococcus lactis* subspecies *lactis* CHCC373 and mutants or variants hereof (DN221-DN226) as described in the following examples. The strains listed were grown from single colonies of the respective strains overnight in 10 ml M17 medium aerobically (+, hatched bars) and anaerobically (−, open bars). The following day, $OD_{600}$. pH and acetoin production were measured.

EXAMPLES

Materials and Methods
1. Bacterial Strains, Media and Growth Conditions

The following lactic acid bacterial strains were used in the examples: *Lactococcus lactis* subspecies *lactis* strains 1FHCY-1, MG1363 and CHCC373 (Chr. Hansen Culture Collection), *Lactococcus lactis* subspecies *lactis* biovar *diacetylactis* DB1341 and *Streptococcus thermophilus* strain CHCC2134 (Chr. Hansen Culture Collection).

As growth media were used: (i) M17 medium (Terzaghi et al. 1975); (ii) the defined phosphate-buffered DN-medium (Dickely et al. 1995) with or without NaAcetate (DN or DN-Ac, respectively). M17 medium was obtained by adding the following ingredients to 1,000 ml of glass-distilled water in a 2-liter flask: polypeptone (BBL, Cockeysville, Md.), 5.0 g; Phytone peptone (BBL), 5.0 g; yeast extract (BBL), 2.5 g; beef extract (BBL), 5.0 g; lactose (May and Baker Ltd., Dagenham, England), 5.0 g; ascorbic acid (Sigma Chemical Co., St. Louis, Mo.), 0.5 g; β-sodium GP (grade II, Sigma Chemical Co.), 19.0 g; and 1.0 M $MgSO_4.7H_2O$ (May and Baker, Ltd.), 1.0 ml. The DN-medium does not contain lipoic acid, but was supplemented with NaFormate at a concentration of 0.6%; and (iii) reconstituted skim milk, RSM containing 9.5% low heat skim milk powder (Milex 240 lh, MD Foods, Denmark).

The strains were cultivated at 30° C. and growth was monitored by measuring the optical density (OD) at 600 nm and/or pH. Anaerobic conditions for growth on agar plates were obtained by incubation in a sealed container using the Anaerocult® A system (Merck, Darmstadt, Germany). In the following, anaerobic growth conditions for cultures in liquid media means cultivation without shaking and aerobic cultivation means growth under shaking.

2. Mutagenesis of *L. lactis*

A single colony of *L. lactis* was inoculated in 10 ml DN-medium and incubated for 16 hours under vigorous shaking. To the outgrown culture 150 µl of ethyl methane sulphonate (EMS, Sigma) was added and the mixture was incubated further under shaking. After 2 hours, 10 tubes each containing 2 ml DN-medium were each inoculated with 0.2 ml of the mutagenized culture. The tubes were incubated until the following day under shaking for phenotypic expression. Sterile glycerol was added to a final concentration of 15% (v/v) and the cultures were stored at −70° C. until use.

3. Determination of Lactate Dehydrogenase Activity

A single colony of *L. lactis* was inoculated in 10 ml M17 medium and cultivated overnight. After cooling for 15 min. on ice, the cells were harvested by centrifugation at 7000 rpm for 5 min. at 4° C., washed in 5 ml ice-cold Ldh assay buffer (50 mM Tris-Acetate pH 6.0, 0.5 mM Fructose-1,6-diphosphate) and resuspended in 1 ml ice-cold Ldh assay buffer. The resuspended cells were transferred to a 5 ml glass tube and sonicated on ice using a Branson Sonifier 250 at the following parameters: timer, 4 min.; duty cycle 25%; output 4. Subsequent to the sonication, the content of the tube was transferred to an ice-cold Eppendorf tube and centrifuged at 15,000×g for 5 min. at 4° C. The supernatant was transferred to a new ice-cold Eppendorf tube. The Ldh specific activity of the cell-free extract was measured at 25° C. in the following manner: 5 µl of cell-free extract was added to 495 µl Ldh assay buffer containing 0.2 mM NADH and 25 mM pyruvate. As control, an assay without pyruvate was used. The conversion of NADH to $NAD^+$ was followed spectrophotometrically over time at 340 nm using a Spectronic® Genesys 5 spectrophotometer. One unit corresponds to the conversion of 1 µmol NADH $min^{-1}$ $ml^{-1}$ cell-free extract. The specific activity is expressed in units/mg protein. For measuring the protein concentration of the cell-free extract, the Bicinchoninic acid (BCA) assay (Pierce, Rockford, U.S.A.) was used with Albumin Standard (Pierce) as protein standard.

4. Determination of *L. lactis* Fermentation End Products

Overnight cultures of the *L. lactis* strains were inoculated in the respective media and incubated for 24 hours under the relevant growth conditions. Samples were collected and analyzed by HPLC and HS-GC for various compounds produced during the cultivation as described by Houlberg (1993, 1995a, 1995b). In certain experiments acetoin was measured as follows: 1 ml culture was transferred to an Eppendorf tube and centrifuged at 15,000×g, 5 min at 4° C. to remove the cells. The supernatant was transferred to a new tube and kept on ice until the acetoin level was measured colometrically using the method of Westerfeld (1945).

Example 1

Acetate Requirement for Growth of *L. lactis*

Initially, the *L. lactis* subspecies *lactis* strains 1FHCY-1 and MG1363 were tested for growth on DN-medium with (DN) or without (DN-Ac) acetate, respectively.

The above mentioned strains were streaked onto DN and DN-Ac agar plates, respectively. The plates were incubated for 24 hours under anaerobic and aerobic conditions, respectively. The results are summarized in Table 1 below:

TABLE 1

| Acetate requirement of 1FHCY-1 and MG1363 | | | | |
|---|---|---|---|---|
| | Aerobic | | Anaerobic | |
| | +Ac | −Ac | +Ac | −AC |
| 1FHCY-1 | +++ | − | +++ | +++ |
| MG1363 | +++ | − | +++ | +++ |

+++: colony size 0.5-1 mm;
−: no growth after prolonged incubation

The tested *L. lactis* strains have an absolute requirement for acetate under aerobic growth conditions.

The wild-type strain *Lactococcus lactis* subspecies *lactis* CHCC373 was selected from the culture collection of Chr.

Hansen A/S, Hørsholm, Denmark and tested for its growth requirement for acetate under aerobic and anaerobic conditions respectively by streaking a liquid culture of the strain onto a series of DN-medium plates containing increasing concentrations of NaAcetate in the range of from 0 to 0.2% (w/v).

Under aerobic conditions weak growth was observed at 0.01% NaAcetate and at 0.02% full growth was observed. No growth was observed at concentrations below 0.005% NaAcetate. Under anaerobic conditions full growth was observed at 0-0.2% NaAcetate.

In the following experiments, DN-medium with 0.1% NaAcetate (DN) or not containing NaAcetate (DN-Ac) was used.

Example 2

Isolation of Pfl Defective Mutants of *Lactococcus lactis* Subspecies *lactis* CHCC373 and *Lactococcus lactis* Subspecies *Lactis* Biovar *diacetylactis* DB1341 and Characterization Hereof 2.1. Isolation of Mutants Mutagenized stocks of the strains CHCC373 and DB1341 were prepared as described above and plated in dilutions onto DN-medium agar plates which were incubated aerobically for 24 to 48 hours. From these plates, 980 colonies of each strain were selected and streaked onto DN and DN-Ac agar plates, respectively and these plates were incubated for 24 hours under anaerobic conditions. Two strains designated DN220 and DN221, respectively from the mutagenized CHCC373 strain and one strain designated DN227 from the mutagenized DB1341 strain which were unable to grow in the absence of acetate under anaerobic conditions were selected.

Chromosomal DNA was isolated from DN220, DN221 and CHCC373, respectively and digested with EcoRI, and the fragment patterns were compared using agarose gel electrophoresis. The fragment patterns showed that both DN220 and DN221 originated from CHCC373. DN221 was selected for further experiments.

Samples of DN220, DN221 and DN227, respectively were deposited with Deutsche Sammlung von Mikroorganismen und Zellkulturen GmbH, Mascheroder Weg 1b, D-38124 Braunschweig, Germany on 26 Jun. 1996 under the respective accession Nos. DSM 11033, DSM 11034 and DSM 11040.

A sample of CHCC 373 was deposited in accordance with the Budapest Treaty, with the same international depository authority, on Feb. 17, 1998 under the accession number DSM 12015.

2.2. Growth of DN221 in M17 Medium and RSM

CHCC373 and DN221 were inoculated in M17 and the cultures were incubated under aerobic and anaerobic conditions, respectively. Under aerobic growth conditions, DN221 and CHCC373 did grow equally well as judged by the $OD_{600}$ and the pH. However, the growth rate of DN221 in M17 under anaerobic conditions was considerably lower than that of CHCC373 and it declined at a lower cell mass. These results showed that absence of acetate in M17 was not the reason for the slower growth rate of the selected mutant strain but indicated that an essential characteristic necessary for anaerobic growth is lacking in DN221 as compared to CHCC373. These results are consistent with the assumption that DN221 has a defect in its Pfl activity resulting in a requirement for acetate and a lower growth rate under anaerobic conditions as compared to CHCC373.

2.3. Analysis of Fermentates for Various End Products

Single colonies of CHCC373 and DN221, respectively were inoculated in M17 and RSM, respectively and these cultures were incubated for 24 hours under anaerobic conditions. Samples were collected taken analyzed for content of fermentation end product compounds according to the above methods.

The results which are summarized in FIGS. 2 and 3 show that formate is not produced by DN221, but is produced by CHCC373 at a high level. This confirms that DN221 lacks Pfl activity This is further confirmed by the low levels of ethanol and acetate produced by DN221 as compared to its parent strain, CHCC373.

Example 3

Isolation of Pfl and Ldh Defective Mutants and Characterization Hereof 3.1. Isolation of Mutants A stock of DN221 was mutagenized as described above under Materials and Methods, and the mutagenized cells were plated in dilutions onto DN-medium agar plates which were incubated aerobically for 24-48 hours. From theses plates, 980 colonies were selected and each colony was streaked onto two DN plates and incubated 24 hours under anaerobic and aerobic conditions, respectively. Two strains (DN222 and DN223) which were unable to grow under anaerobic conditions were selected.

Chromosomal DNA was isolated from DN222, DN223 and CHCC373, respectively and digested with EcoRI. The fragment patterns were compared using agarose gel electrophoresis. The fragment patterns showed that both DN222 and DN223 originate from CHCC373.

Samples of DN222 and DN223, respectively were deposited with Deutsche Sammlung von Mikroorganismen and Zellkulturen GmbH, Mascheroder Weg 1b, D-38124 Braunschweig, Germany on 26 Jun. 1996 under the respective accession Nos. DSM 11035 and DSM 11036.

3.2. Testing for Lactate Dehydrogenase (Ldh) Activity

The Ldh activity of DN221, DN222, DN223 and CHCC373 was analyzed in accordance with the method described above, and the results are shown in Table 3.1 below.

TABLE 3.1

Ldh activity of DN221, DN222, DN223 and CHCC373

| Strain | CHCC373 | DN221 | DN222 | DN223 |
|---|---|---|---|---|
| Spec. activity [a] NADH oxidase | 0.30 | 0.28 | 0.12 | 0.59 |
| Spec. activity [b] Ldh | 21.40 | 19.10 | 16.00 | 0.70 |
| % Ldh act. | 100.00 | 89.00 | 75.00 | 3.00 |

[a] units/mg protein; units, μmol NAD+ $min^{-1}$ $ml^{-1}$ extracts. Assay without pyruvate.
[b] as [a] but assay with pyruvate.

These results show that DN223 has a defect in the Ldh activity having only 3% of the activity of CHCC373, whereas DN222 has a Ldh activity similar to that of CHCC373. Thus it can be concluded that DN223 is Pfl and Ldh defective.

3.2. Growth in M17 and Formation of End Products Under Aerobic Conditions

Single colonies of CHCC373, DN221, DN222 and DN223, respectively were inoculated in M17 and incubated under aerobic conditions. The results of measurements of $OD_{600}$ and pH for the outgrown cultures are shown in table 3.2 below.

TABLE 3.2

OD$_{600}$ and pH of CHCC373, DN221, DN222 and DN223

|  | CHCC373 | DN221 | DN222 | DN223 |
|---|---|---|---|---|
| OD [a] | 3.26 ± 0.16 | 3.16 ± 0.02 | 1.7 ± 0.08 | 3.22 ± 0.16 |
| pH [b] | 5.7 ± 0.06 | 5.71 ± 0.08 | 5.84 ± 0.16 | 6.21 ± 0.08 |

[a] a single colony was inoculated in 10 ml M17 medium and cultivated for 24 hours followed by measuring the OD$_{600}$.
[b] as [a] except that the pH was measured.

Under these conditions DN221, DN223 and CHCC373 had similar growth yields as judged by the OD$_{600}$ measurements. However, the OD$_{600}$ of DN222 was only about half the OD$_{600}$ of the wild-type strain. DN221 and DN222 both acidified the medium to the same pH level, whereas DN223 only acidified the medium slightly, even though the growth as judged by the OD$_{600}$ was similar to that of CHCC373, confirming that DN223 is Ldh defective.

Overnight cultures from single colonies of CHCC373, DN221, DN222 and DN223 were inoculated in M17 and RSM were incubated for 24 hours under aerobic conditions and samples were taken for analysis of end products as described above. Results from the analysis are shown in Table 3.3 below.

TABLE 3.3

End product formation in M17

|  | AA mM* | EtOH mM* | DAc mM* | HMEK mM* | ALA mM* | HAc mM* | Lacto mM* | HLac mM* |
|---|---|---|---|---|---|---|---|---|
| M17 | 0.02 | 0.05 | 0.00 | 0.2 | 0.00 | 1.7 | 5.5 | 0.00 |
| CHCC373 | 0.15 | 0.06 | 0.02 | 2.2 | 0.03 | 23.3 | 0.00 | 24.2 |
| DN221 | 0.15 | 0.08 | 0.02 | 2.7 | 0.03 | 25.0 | 0.00 | 24.2 |
| DN222 | 0.12 | 0.03 | 0.03 | 1.6 | 0.02 | 16.7 | 0.00 | 22.0 |
| DN223 | 0.12 | 0.32 | 0.07 | 14.2 | 0.15 | 18.3 | 0.00 | 4.4 |

*see abbreviation below
Abbreviations:
AA acetaldehyde
DAc diacetyl
HAc acetic acid
HMEK acetoin
ALA acetolactate
EtOH ethanol
HLac lactic acid
Lacto lactose CHCC373 produces almost equal amounts of acetate and lactate. Under aerobic conditions DN221 produce similar amounts of end products as does CHCC373. DN222 produces less acetate and equal amounts of lactate as does CHCC373. The defect in DN222 is unknown. DN223 produces very small amounts of lactate as compared to CHCC373. DN223 converted the major part of pyruvate to acetoin instead of lactate. This change in pyruvate catabolism is also reflected in that the aroma compound diacetyl was increased 3-4 fold as compared to CHCC373 and in that about 55% of the catabolized pyruvate passed via α-acetolactate (ALA) to acetoin (HMEK). The percentage is probably higher as the butanediol production was not measured.

Example 4

Isolation and Characterization of Spontaneous Mutants of DN223

4.1. Isolation of Mutants

A liquid culture was made from a single colony of DN223 and incubated under aerobic conditions overnight. Approximately 10$^8$ cells were transferred to DN-medium agar plates which were incubated under anaerobic conditions. Three strains designated DN224, DN225 and DN226 were isolated based on their ability to grow under anaerobic conditions. The three strains are all mutants or variants of DN223 having regained the ability to convert NADH to NAD$^+$ under anaerobic conditions either by mutations in secondary systems to Ldh and Pfl or by reversion of the Pfl or the Ldh defect.

Chromosomal DNA was isolated from DN224, DN225, DN226 and CHCC373, respectively and digested with EcoRI. The fragment patterns were compared using agarose get electrophoresis. The fragment patterns showed that DN224, DN225 and DN226 all originate from CHCC373.

Samples of DN224, DN225 and DN226, respectively were deposited with Deutsche Sammlung von Mikroorganismen and Zellkulturen GmbH, Mascheroder Weg 1b, D-38124 Braunschweig, Germany on 26 Jun. 1996 under the respective accession Nos. DSM 11037, DSM 11038 and DSM 11039.

4.2. Growth in M17 and Acetoin Formation

Single colonies of CHCC373, DN221, DN222, DN223, DN224 and DN226, respectively were inoculated in M17 and incubated overnight under anaerobic and aerobic conditions, respectively. The final OD$_{600}$ and pH were measured and samples were collected and analyzed for content of acetoin. The results are shown in FIG. 4.

All of the tested strains, except DN222, grew well under aerobic conditions. Under anaerobic conditions, DN221, DN222 and DN223 had severe growth defects, DN223 being the most growth inhibited strain. Measurements of the pH reflected the growth pattern of the strains except for DN223, DN224 and DN226 grown under aerobic conditions. These results showed that DN224 and DN226 have reduced acidifying capacity compared to CHCC373, possibly caused by a defect in Ldh.

Under both aerobic and anaerobic conditions DN225 has a growth yield equal to CHCC373 indicating that this strain had lost the Ldh defect.

Under aerobic conditions, the strains DN223, DN224 and DN226 produced acetoin in the range of 1100-1200 ppm which is 4-6 times more than the other strains (about 200 ppm). Under anaerobic conditions, DN223 produced about 10-fold more acetoin than the strains DN222 and CHCC373, even though almost no growth was observed as judged by the OD$_{600}$ value. DN224 and DN226 produced more than 10 ppm acetoin under anaerobic conditions, which is considerably more than the 2.5 ppm produced by CHCC373 and DN222. The high concentrations of acetoin produced by the three strains indicates that these strains have the potential of producing high amounts of diacetyl.

Among the above spontaneous mutants, DN224 was selected for further studies of fermentation end product formation.

4.3. Growth in RSM and Formation Herein of End Products

Single colonies of CHCC373, DN221, DN223 and DN224 were inoculated in 10 ml M17 and incubated overnight. The final OD$_{600}$ and pH were measured. The results are shown in Table 4.1 below.

TABLE 4.1

Growth (OD$_{600}$) of CHCC373, DN221, DN223 and DN224 in M17

|  | OD$_{600}$ | pH |
|---|---|---|
| CHCC373 | 3.34 | 5.7 |
| DN221 | 3.22 | 5.72 |

TABLE 4.1-continued

Growth (OD$_{600}$) of CHCC373, DN221, DN223 and DN224 in M17

|  | OD$_{600}$ | pH |
|---|---|---|
| DN223 | 3.44 | 6.29 |
| DN224 | 3.28 | 6.29 |

Subsequently 2×200 µl of each culture was transferred to 2×10 ml RSM and incubated over night under aerobic and anaerobic conditions, respectively. pH was measured and results are shown in Table 4.2 below.

TABLE 4.2

Growth (pH) of CHCC373, DN221, DN223 and DN224 in RSM

|  | pH | |
|---|---|---|
|  | Anaerobic | Aerobic |
| milk | 6.82 | 6.8 |
| CHCC373 | 4.37 | 5.01 |
| DN221 | 5.02 | 5.23 |
| DN223 | 6.56 | 6.08 |
| DN224 | 5.13 | 6.06 |

The growth in RSM under aerobic conditions, as judged by pH, appears to be as in M17 indicating, that the acidifying capacity is independent of the media used.

From all cultures samples were taken for analysis of end products. The results are shown in Table 4.3 below.

None of the strains fermented citrate as would be expected of a *L. lactis* subspecies *lactis*. The wild-type strain CHCC373 grown under aerobic conditions produced relatively high amounts of acetoin, diacetyl, α-acetolactate, acetaldehyde and acetate, but relatively low amounts of ethanol and lactate as compared to the production hereof under anaerobic conditions.

From the results obtained from DN224, it can be seen that the levels of the different aroma compounds have changed significantly during anaerobic growth. The level of acetaldehyde was increased about 8-fold, the diacetyl precursor α-acetolactate had increased more than 10-fold as compared to the level hereof of CHCC373.

However, it is assumed that the potential for diacetyl production is much higher, as the amount of acetoin produced by DN224 compared to the amount of acetoin produced by CHCC373 is significantly higher. The increase of formate, ethanol and acetate production and the reduction of lactate production indicates that DN224 has lost the defect in Pfl but is still Ldh defective. This is further verified by the fact that DN224 grows under anaerobic conditions which the Pfl and Ldh defective strain DN223 does not.

Example 5

Detection of Acetate Requirement for Growth of *Streptococcus thermophilus*

Single colonies of *Streptococcus thermophilus* CHCC2134 was streaken onto plates of DN agar containing lactose (5 g/L), Na-formiate (20 mg/L) and with and without acetate. The plates were incubated for 48 hours at 37° C. under aerobic and anaerobic conditions, respectively. Growth occurred as summarized in Table 5.1 below:

TABLE 4.3

End product formation in RSM

|  |  | HCit* mM | HAc* mM | Lacto* mM | HLac* mM | AA* mM | EtOH* mM | DAc* mM | HMEK* mM | ALA* mM | MeFo* mM |
|---|---|---|---|---|---|---|---|---|---|---|---|
| RSM |  | 9.5 | 0 | 132 | 1. | 0.1 | 0 | 0 | 0 | 0.1 | 0.2 |
| RSM |  | 9.3 | 0 | 131 | 1.1 | 0.01 | 0 | 0 | 0.16 | 0.01 | 0.2 |
| CHCC373 | aerobic | 9.5 | 5 | 109 | 46.7 | 0.08 | 0.06 | 0.13 | 10.93 | 0.24 | 0.13 |
| CHCC373 | aerobic | 9.5 | 5 | 108 | 47.8 | 0.08 | 0.07 | 0.14 | 11.47 | 0.21 | 0.11 |
| CHCC373 | anaerobic | 8.1 | 1.7 | 96 | 70 | 0.02 | 0.93 |  | 0.14 | 0 | 1.09 |
| CHCC373 | anaerobic | 9.5 | 1.7 | 106 | 76.7 | 0.02 | 0.88 | 0 | 0 | 0 | 1.35 |
| DN221 | aerobic | 9.5 | 3.3 | 117 | 38.9 | 0.05 | 0 | 0.02 | 1.11 | 0.02 | 0.01 |
| DN221 | aerobic | 9.5 | 3.3 | 117 | 38.9 | 0.05 | 0.02 | 0.02 | 1.07 | 0.02 | 0.01 |
| DN221 | anaerobic | 9 | 1.7 | 114 | 51.1 | 0.05 | 0.36 | 0.01 | 0.39 | 0.01 | 0.11 |
| DN221 | anaerobic | 8.6 | 1.7 | 109 | 46.7 | 0.05 | 0.35 | 0.01 | 0.22 | 0.01 | 0.11 |
| DN223 | aerobic | 9 |  | 119 | 6.6 | 0.04 | 0.05 | 0.12 | 10.54 | 0.21 | 0.13 |
| DN223 | aerobic | 10 | 5 | 120 | 6.7 | 0.05 | 0.05 | 0.13 | 10.73 | 0.2 | 0.13 |
| DN223 | anaerobic | 10 | 1.7 | 131 | 3.3 | 0.01 | 0.06 | 0.01 | 0.3 | 0.01 | 0.28 |
| DN223 | anaerobic |  | 1.7 | 122 | 3.3 | 0.01 | 0.05 | 0.01 | 0.36 | 0.01 | 0.26 |
| DN224 | aerobic | 10 | 5 | 123 | 7.8 | 0.05 | 0.04 | 0.13 | 10.84 | 0.21 | 0.15 |
| DN224 | aerobic | 9.5 | 5 | 119 | 6.7 | 0.05 | 0.04 | 0.13 | 10.42 | 0.21 | 0.13 |
| DN224 | anaerobic | 9 | 6.7 | 115 | 15.6 | 0.14 | 13.19 | 0.01 | 4.14 | 0.09 | 12.52 |
| DN224 | anaerobic | 2 | 6.7 | 119 | 16.7 | 0.16 | 13.83 | 0.01 | 3.68 | 0.08 | 13.35 |

*see abbreviations below

Abbreviations:
AA acetaldehyde
DAc diacetyl
HAc acetic acid
HLac lactic acid
Lacto Lactose
ALA acetolactate
EtOH ethanol
HCit citrate
HMEK acetoin
MeFo formate

TABLE 5.1

Acetate requirement of *Streptococcus thermophilus* CHCC2134

|  | Aerobic | Anaerobic |
|---|---|---|
| With acetate | ++ | +++ |
| Without acetate | − | +++ |

++: colony size 0.1-0.5 mm;
+++: colony size 0.5-2 mm;
−: no growth after prolonged incubation Since acetate is required for growth at aerobic conditions, the basis exists for the isolation of a mutant strain of *Streptococcus thermophilus* that has a requirement for acetate under anaerobic conditions, i.e. a Pfl⁻ mutant of that species. Such a mutant strain could, in analogy with the above, be used as the starting material in the isolation of a second mutant strain being incapable of growing under anaerobic conditions, i.e. a Pfl⁻/Ldh⁻ mutant.

REFERENCES

1. Dickely F, Nilsson D, Hansen E B, Johansen E. 1995. Isolation of *Lactococcus lactis* nonsense suppressors and construction of a food-grade cloning vector. Molec. Microbiol., 15, 839-847.
2. Gasson M J, Benson K, Swindell S, Griffin H. 1996. Metabolic engineering of the *Lactococcus lactis* diacetyl pathway. Lait, 76, 33-40.
3. Houlberg U. 1993. HPLC analysis: Determination of acids & carbohydrates in liquid fermentation media using internal standard. Analytical Procedure 1009, Chr. Hansen A/S.
4. Houlberg U. 1995a. HSGC-In situ derivatization of acids in fermentates for physiological investigations. Technical Report 785, Chr. Hansen A/S.
5. Houlberg U. 1995b. HSGC-Determination of volatile organic compounds and α-acetolactic acid.
6. Hugenholtz J. 1993. Citrate metabolism in lactic acid bacteria. FEMS Microbiology Reviews, 12, 165-178.
7. Knappe J. 1987. Anaerobic dissimilation of pyruvate. In F. C. Neidhardt (ed.) *Escherichia coli* and *Salmonella typhimurium*. Cellular and Molecular Biology. pp 151-155.
8. Platteeuw C, Hugenholtz J, Starrenburg M, van Alen-Boerrigter I, De Vos W M. 1995. Metabolic engineering of *Lactococcus lactis*: Influence of the overproduction of α-acetolactate synthetase in strains deficient in lactate dehydrogenase as a function of culture conditions. Appl. Environ. Microbiol., 61, 3967-3971.
9. Snoep J L. 1992. Regulation of pyruvate catabolism in *Enterococcus faecalis*. Ph. D. thesis, University of Amsterdam, Netherlands.
10. Terzaghi B E, Sandine W E. 1975. Improved medium for the lactic streptococci and their bacteriophages. Appl. Microbiol., 29, 807-813.
11. Westerfeld W W. 1945. A calorimetric determination of blood aceton. J. Biol. Chem., 16, 495-502

The invention claimed is:

1. An isolated bacterium which is *Lactococcus lactis* subspecies *lactis* DN224, deposited under the accession number DSM 11037, or a non-naturally occurring *Lactococcus lactis* subspecies *lactis* bacterium derived by mutation thereof, said bacterium being lactate dehydrogenase (Ldh) defective but having pyruvate formate-lyase (Pfl) activity, which bacterium is capable of growing anaerobically.

2. An isolated bacterium, which is *Lactococcus lactis* subspecies *lactis* strain DN224 deposited under the accession number DSM 11037, or a strain having essentially all of the characteristics of DSM 11037.

3. The bacterium of claim 1, which is *Lactococcus lactis* subspecies *lactis* strain DN224 deposited under the accession number DSM 11037, or a strain having all of the characteristics of DSM 11037.

4. An isolated bacterium which is *Lactococcus lactis* subspecies *lactis* strain DN226 deposited under the accession number DSM 11039, or a strain having all of the characteristics of DSM 11039.

5. The bacterium of claim 1 which has a reduced rate of acid production, relative to that of CHCC373 (DSM 12015), when cultivated under anaerobic conditions in M17 medium or in reconstituted skin milk.

6. The bacterium of claim 1, which is capable of anaerobic alpha-acetolactate production which is at least 100% greater than of CHCC373 under the same conditions.

7. The bacterium of claim 1, which is capable of anaerobic production of an alpha-acetolactate-derived metabolite which is at least 100% greater than that of CHCC373 (DSM 12015) under the same conditions.

8. The bacterium of claim 7 in which the metabolite is acetaldehyde.

9. The bacterium of claim 7 in which the metabolite is acetoin.

10. The bacterium of claim 9 in which at least 15% of pyruvate being catabolized is converted to acetoin.

11. The bacterium of claim 1 which is capable of an increased aerobic production of formate, ethanol and acetate, and reduced production of lactate, relative to that of CHCC373 (DSM 12015), when cultivated under the same conditions.

12. The bacterium of claim 1 which, grown anaerobically in RSM medium, is capable of producing in excess of 1mM acetoin and/or in excess of 10 mM formate.

13. A method of producing a food product, the method comprising adding to the food product starting materials a culture of a lactic acid bacterium selected from the group consisting of the lactic acid bacterium of claim 1.

14. A method of producing a lactic acid bacterial metabolite, the method comprising cultivating a lactic acid bacterium according to claim 1 under conditions where the metabolite is produced, and, if required, isolating the metabolite from the culture.

15. A lactic acid bacterial starter culture composition comprising a lactic acid bacterium of claim 1.

16. A method of obtaining a lactic acid bacterium according to claim 1 which comprises screening spontaneous, chemically induced, or ultraviolet light-induced mutants of DN224 and identifying mutants which are Ldh defective and retain Pfl activity.

* * * * *